United States Patent
Yu et al.

(10) Patent No.: US 9,283,551 B2
(45) Date of Patent: Mar. 15, 2016

(54) CATALYSTS FOR CONVERTING SYNGAS INTO LIQUID HYDROCARBONS AND METHODS THEREOF

(71) Applicant: Mississippi State University, Starkville, MS (US)

(72) Inventors: Fei Yu, Starkville, MS (US); Qiangu Yan, Starkville, MS (US); William Batchelor, Auburn, AL (US)

(73) Assignee: Mississippi State University Research and Technology Corporation, Starkville, MS (US)

( * ) Notice: Subject to any disclaimer, the term of this patent is extended or adjusted under 35 U.S.C. 154(b) by 0 days.

(21) Appl. No.: 14/162,606

(22) Filed: Jan. 23, 2014

(65) Prior Publication Data

US 2016/0038923 A1 Feb. 11, 2016

Related U.S. Application Data

(60) Provisional application No. 61/849,253, filed on Jan. 23, 2013.

(51) Int. Cl.
| | |
|---|---|
| *B01J 29/46* | (2006.01) |
| *B01J 27/22* | (2006.01) |
| *C07C 45/50* | (2006.01) |
| *C07C 51/10* | (2006.01) |
| *C07C 29/157* | (2006.01) |

(52) U.S. Cl.
CPC *B01J 29/46* (2013.01); *B01J 27/22* (2013.01); *C07C 29/157* (2013.01); *C07C 45/50* (2013.01); *C07C 51/10* (2013.01)

(58) Field of Classification Search
CPC .................................. B01J 29/72; B01J 27/22
See application file for complete search history.

(56) References Cited

U.S. PATENT DOCUMENTS

| | | | |
|---|---|---|---|
| 4,096,163 A | 6/1978 | Chang et al. | |
| 4,188,336 A | 2/1980 | Chang | |
| 4,279,830 A | 7/1981 | Haag et al. | |
| 4,618,412 A * | 10/1986 | Hudson et al. | ........... 208/59 |
| 5,140,049 A * | 8/1992 | Fiato | ........... C07C 1/12 518/700 |
| 5,714,657 A * | 2/1998 | deVries | ........... C07C 1/0485 518/702 |
| 7,384,987 B2 * | 6/2008 | Iordache-Cazana | .. C07C 29/156 518/700 |
| 7,943,673 B2 | 5/2011 | Kibby | |

(Continued)

OTHER PUBLICATIONS

Odell et al. J. Catal. 1994, 147, 358.*
Woo et al. J. Catal. 1993, 142, 672.*

(Continued)

*Primary Examiner* — Jafar Parsa
*Assistant Examiner* — Medhanit Bahta
(74) *Attorney, Agent, or Firm* — Stites & Harbison PLLC; Richard S. Myers, Jr.

(57) ABSTRACT

The presently-disclosed subject matter includes methods for producing liquid hydrocarbons from syngas. In some embodiments the syngas is obtained from biomass and/or comprises a relatively high amount of nitrogen and/or carbon dioxide. In some embodiments the present methods can convert syngas into liquid hydrocarbons through a one-stage process. Also provided are catalysts for producing liquid hydrocarbons from syngas, wherein the catalysts include a base material, a transition metal, and a promoter. In some embodiments the base material includes a zeolite-iron material or a cobalt-molybdenum carbide material. In still further embodiments the promoter can include an alkali metal.

23 Claims, 5 Drawing Sheets

(56) References Cited

U.S. PATENT DOCUMENTS

2009/0293359 A1* 12/2009 Simmons et al. ............ 48/127.7
2010/0197959 A1* 8/2010 Johnston et al. ............ 560/265

OTHER PUBLICATIONS

Kegong Fang, Debao Li, Minggui Lin, Minglin Xiang, Wei Wei, Yuhan Sun, A short review of heterogeneous catalytic process for mixed alcohols synthesis via syngas, Catalysis Today 147 (2009) 133-138.
Xiang, Minglin, Li, Debao, Xiao, Haicheng, Zhang, Jianli, Qi, Huijie, Li, Wenhuai, Zhong, Bing and Sun, Yuhan, Synthesis of higher alcohols from syngas over Fischer-Tropsch elements modified K/β-Mo2C catalysts, Fuel, 87, 2008, pp. 599-603.
Xiao-Hui Wang, Ming-Hui Zhang, Wei Li, Ke-Yi Tao, Synthesis and characterization of cobalt—molybdenum bimetallic carbides catalysts, Catalysis Today 131 (2008) 111-117.
Korlann, S., Diaz, B. and Bussell, M.E.,; Synthesis of Bulk and Alumina-Supported Bimetallic Carbide and Nitride Catalysts; Chem. Mater.,14, 2002, pp. 4049-4055.
Tian-Cun Xiao, Andrew P.E York, Hamid Al-Megren, Cliff V Williams, Hai-Tao Wang, Malcolm L.H Green, Preparation and Characterisation of Bimetallic Cobalt and Molybdenum Carbides, Journal of Catalysis, 202,100-109 2001.
Liang, C., Ying, P. and Li, C.,; Nanostructured β-Mo2C Prepared by Carbothermal Hydrogen Reduction on Ultrahigh Surface Area Carbon Material; Chem. Mater.,14, 2002, pp. 3148-3155.
Liang, C., Ma, W., Feng, Z. and Li, C.,; Nanostructured β-Mo2C Prepared by Carbothermal Hydrogen Reduction on Ultrahigh Surface Area Carbon Material; Carbon, 41, 2003, pp. 1833-1839.
Liang, C., Tian, F., Li, Z., Feng, Z., Wei, Z. and Li, C.,; Preparation and Adsorption Properties for Thiophene of Nanostructured W2C on Ultrahigh-Surface-Area Carbon Materials; Chem. Mater.,15, 2003, pp. 4846-4853.
Wang, Xiao-Hui, Zhang, Ming-Hui, Li, Wei and Tao, Ke-Yi, Synthesis and characterization of cobalt—molybdenum bimetallic carbides catalysts, Catalysis Today, 131, 2008, pp. 111-117.
Han, J., X. He, R. Li, C. Wan, Q. Yan, and F. Yu*. 2014. Oxygen removal from syngas by catalytic oxidation of copper catalyst. Journal of the Energy Institute. 87:246-252.
Yan, Q., Y. Lu, C. Wan, J. Han, J. Rodriguez, J. Yin, and F. Yu*. 2014. Synthesis of Aromatics-rich Gasoline Range Hydrocarbons from Biomass-derived Syngas over Pd-promoted Fe/HZSM-5 Catalyst. Energy and Fuels. 28 (3):2027-2034.
Yan, Q., C. Wan, J. Street, D. Yan, J. Han, and F. Yu*. 2013. Catalytic Removal of Oxygen from Biomass-derived Syngas. Bioresource Technology. 147:117-123.
Yan, Q., C. Wan, J. Liu, J. Gao, F. Yu, J. Zhang, and Z. Cai. 2013. Iron Nanoparticles in situ Encapsulated in Biochar-based Carbon as an Effective Catalyst for Conversion of Biomass-derived Syngas to Liquid Hydrocarbons; Green Chemistry; 15; pp. 1631-1640.
Yan, Q., F. Yu, Z. Cai, and J. Zhang. 2012. Catalytic upgrading nitrogen-riched wood syngas to liquid hydrocarbon mixture over a Fe—Pd/ZSM-5 catalyst. Biomass and Bioenergy. 47: 469-473.
Yan, Q., F. Yu, J. Liu, J. Street, J. Gao, Z. Cai, and J. Zhang. 2012. Catalytic Conversion Wood Syngas to Synthetic Aviation Turbine Fuels over a Multifunctional Catalyst. Bioresource Technology. 127:281-290.
Woo, et al.,; Structure and Distribution of Alkali Promoter in K/MoS2 Catalysts and Their Effects on Alcohol Synthesis from SyngaJ. Catal. 1993,142,672.
Epling, W S.; Hoflund, G B.; Hart, W. M.; Minahan, D. M.; Reaction and Surface Characterization Study of Higher AlcoholSynthesis Catalysts; J. Catal.1997,169,438.
Girardon, et al.; Cobalt dispersion, reducibility, and surface sites in promoted silica-supported Fischer-Tropsch catalysts J. Catal. 2007 248 143.
Jo-Yong Park, Yun-Jo Lee, Ki-Won Jun, Jong Wook Bae, Nagabhatla Viswanadham, Young Ho Kim, Direct conversion of synthesis gas to light olefins using dual bed reactor, Journal of Industrial and Engineering Chemistry, 2009, 15( 6), 25 847-853.
B. Shi, B.; Davis, B H., Fischer-Tropsch synthesis accounting for chain-length related phenomena; Appl. Catal. A: General, 2004, 277, 61-69.
Qiangu Yan, et al., Synthesis Gas to Hydrocarbons over CuO—CoO—Cr2O3—H+-ZSM-5 Bifunctional Catalysts, J. Phys. Chem. C, 2008, 112 (31), pp. 11847-11858.
Mysov, V. M.; Reshetnikov, S. I.; Stepanov, V. G.; Ione, K. G., Synthesis gas conversion into hydrocarbons (gasoline range) over bifunctional zeolite-containing catalyst experimental study and mathematical modelling, Chem. Eng. J. 2005 107 63.
Comelli, R. A.; Figoli, N. S., Hydrocarbon production from synthesis gas over ZnO—Cr2O3+SA physical mixtures and Pd/SA impregnated catalysts, React. Kinet. Catal. Lett.1994, 52, 139.
Xu, D., H Duan, et al., Investigation on the Fischer-Tropsch Synthesis with Nitrogen-Containing Syngas over CoPtZrO2Al2O3 Catalyst, Energy Fuels, 2006, 20(3): 955-958.
Jess, A., R. Popp, et al., Fischer-Tropsch-synthesis with nitrogen-rich syngas Fundamentals and reactor design aspects; (1999), Applied Catalysis A: General,186(1-2): 321-342.
Martinez, Agustin; Rollán, Joan; Arribas, Maria A.; Cerqueira, Henrique S.; Costa, Alexandre F. and Aguiar, Eduardo Falabella S., A detailed study of the activity and deactivation of zeolites in hybrid CoSiO2-zeolite Fischer-Tropsch catalysts, J. Catal. 2007,249, 162.
Girardon, J.-S.; Quinet, E.; Griboval-Constant, A.; Chernavskii, P.A.; Gengembre, L. and Khodakov, A.Y., Cobalt dispersion, reducibility, and surface sites in promoted silica-supported Fischer-Tropsch catalysts, J. Catal. 2007, 248, 143.
Gormley, R. J.; Rao, V. U. S.; Anderson, R. R.; Schehl, R. R. and Chi, R. D. H., Secondary reactions on metal-zeolite catalysts used in synthesis gas conversion, J. Catal. 1988,113, 193.
Mills, G. Alex, Status and future opportunities for conversion of synthesis gas to liquid fuels, Fuel, 1994, 73, 1243.
Morales, Fernando; de Smit, Emiel; de Groot, Frank M.F.; Visser, Tom and Weckhuysen, Bert M., Effects of manganese oxide promoter on the CO and H2 adsorption properties of titania-supported cobalt Fischer-Tropsch catalysts, J. Catal. 2007, 246, 91.
Liu, Zhong-Wen; Li, Xiaohong; Asami, Kenji and Fujimoto,K., High performance Pd-beta catalyst for the production of gasoline-range iso-paraffins via a modified Fischer-Tropsch reaction, Appl. Catal. A: General 2006, 300, 162.
Dry, M.E., The Fischer-Tropsch process 1950-2000, Catal. Today, 2002, 71, 227.
Khodakov, A.Y.; Chu, W. and Fongarland, P., Advances in the Development of Novel Cobalt Fischer-Tropsch Catalysts for Synthesis of Long-Chain Hydrocarbons and Clean Fuels, Chem. Rev., 2007,107, 1692.
Espinoza, R.L.; Steynberg, A.P.; Jager, B. and Vosloo, A.C., Low temperature Fischer-Tropsch synthesis from a Sasol perspective, Appl. Catal. A: General1999,186, 13.
Bedel, L.; Roger, Anne-Cécile; Rehspringer, Jean-Luc; Zimmermann, Yvan and Kiennemann, A., La(1-y) Co0.4Fe0.6O3-δ perovskite oxides as catalysts for Fischer-Tropsch synthesis, J. Catal. 2005, 235, 279.
Buchang Shi, Burtron H. Davis, Fischer-Tropsch synthesis: The paraffin to olefin ratio as a function of carbon number, Catalysis Today, 2005,106( 1-4), 129-131.
Patzlaff, J.; Liu, Y.; Graffmann, C. and Gaube, Studies on product distributions of iron and cobalt catalyzed Fischer-Tropsch synthesis, J., Appl. Catal. A: General 1999,186, 109.
Rightor, Edward G.; Tzou, Ming-Shin and Pinnavaia, Thomas J. Iron oxide pillared clay with large gallery height_Synthesis and properties as a Fischer-Tropsch catalyst, J. Catal. 1991,130, 29.
Dictor, Ronald A. and Bell, Alexis T. Fischer-Tropsch synthesis over reduced and unreduced iron oxide catalysts, J. Catal. 1986, 97, 121.
Qiangu Yan, Fei Yu, Jian Liu, Jason Street, Jinsen Gao, Zhiyong Cai, Jilei Zhang, Catalytic conversion wood syngas to synthetic aviation turbine fuels over a multifunctional catalyst, Bioresource Technology, 127, (2013), 281-290.

(56) References Cited

OTHER PUBLICATIONS

Jian Li, Yisheng Tan, Qingde Zhang, Yizhuo Han, Characterization of an HZSM-5/MnAPO-11 composite and its catalytic properties in the synthesis of high-octane hydrocarbons from syngas, Fuel 89 (2010) 3510-3516.

Simard, F.; Sedrán, U. A.; SepúOlveda, J.; Figoli, N. S.; de Lasa, H. ZnO—Cr2O3 + ZSM5 Catalyst with Very Low Zn/Cr ratio for the Transformation of Synthesis Gas to Hydrocarbons. Appl. Catal.1995, 125, 81.

Yingying Yu, Yiming Xu, Dang-guo Cheng, Yingcai Chen, Fengqiu Chen, Xiaoyong Lu, Yiping Huang, Songbo Ni, Transformation of syngas to light hydrocarbons over bifunctional CuO—ZnO/SAPO-34 catalysts: the effect of preparation methods, Reac Kinet Mech Cat (2014) 112:489-497.

Tomoyuki Inui, Takashi Hagiwara and Yoshinobu Takegami, Selective Hydrocarbon Synthesis from Syngas on Composite Catalysts of Modified Methanol-Synthesis Catalysts and ZSM-5 Zeolites, J. Japan Petrol. Inst., 27, (3), (1984) 228-235.

Xiaohong Li, Mengfei Luo, Kenji Asami, Direct synthesis of middle iso-paraffins from synthesis gas on hybrid catalysts, Catalysis Today 89 (2004) 439-446.

Simard, F.; Mahay, A.; Ravella, A.; Jean, G.; de Lasa, H., Pseudoadiabatic catalytic reactor operation for the conversion of synthesis gas into hydrocarbons (gasoline range), Ind. Eng. Chem. Res. 1991; 30, 1448.

Javier Erena, José M. Arandes, Javier Bilbao, Martin Olazar1 and Hugo I. de Lasa, Effect of the operating conditions on the conversion of syngas into liquid hydrocarbons over a Cr2O3—ZnO/ZSM5 bifunctional catalyst, J. Chem. Technol. Biotechnol. 1998, 72, 190-196.

Maria Kulawska, Maria Madej-Lachowska, Copper-zinc catalysts in hydrogenation of carbon monoxide, Chemical and Process Engineering 2013, 34 (4), 479-496.

Zaidi, H. A. and Pant, K. K., Catalytic conversion of methanol to gasoline range hydrocarbons, Catal. Today 2004, 96, 155.

Campbell, S. M.; Bibby, D. M.; Coddington, J. M. and Howe, R. F., Dealumination of HZSM-5 Zeolites II. Methanol to Gasoline Conversion, J. Catal. 1996,161, 350.

Odell, A. L.; Coddington, J. M. and Liddell, M. J., An Attempt to Distinguish Between CH3-Type and CH2-Type Species as Chain-Extending Intermediates in the Conversion of Methanol to Gasoline over the Catalyst H-ZSM-5, J. Catal. 1994,147, 358.

Tau, Li-Min; Fort, Arthur W.; Bao, Shiqi and Davis, Burtron H., Methanol to gasoline 14C tracer studies of the conversion of methanolhigher alcohol mixtures over ZSM-5, Fuel Proc. Tech. 1990, 26, 209.

Amit C. Gujar, Vamshi Krishna Guda, Michael Nolan, Qiangu Yan, HosseinToghiani, Mark G. White,Reactions of methanol and higher alcohols over H-ZSM, Applied Catalysis A: General, vol. 363, 2009, pp. 115-121.

Levy, R.B. and Boudart, M., Platinum-like behavior of tungsten carbide in surface catalysis. Science, 181, 1973, pp. 547-549.

Ribeiro, F.H., Boudart, M., DallaBetta, R.A. and Iglesia, E., Catalytic reactions of normal-alkanes on beta-W2C and WC—the effect of surface oxygen on reaction pathways, J. Catal., 130, 1991, pp. 498-513.

Cheng, Jinmin and Huang, Wei,;Effect of cobalt (nickel) content on the catalytic performance of molybdenum carbides in dry-methane reforming; Fuel Processing Technology, 91, (Feb. 2010), pp. 185-193.

Borowiechi, T. and Golebiowski, A., Influence of molybdenum and tungsten additives on the properties of nickel steam reforming catalysts, Catal. Lett.25, 1994, pp. 309-313.

LaMont, D.C. and Thomson, W.J., The influence of mass transfer conditions on the stability of molybdenum carbide for dry methane reforming, Appl. Catal. A,274, 2004, pp. 173-178.

Moreno-Castilla, C., Alvarez-Merino, M.A., Carrasco-Marin, F., Fierro, J.L.G., Tungsten and tungsten carbide supported on activated carbon: Surface structures and performance for ethylene hydrogenation, Langmuir, 2001, 17 (5), pp. 1752-1756.

Woo, H.C., Park, K.Y., Kim, Y.G., Nam, I.S., Chung, J.S. and Lee, J.S., Mixed alcohol synthesis from carbon-monoxide and dihydrogen over potassium-promoted molybdenum carbide catalysts. Appl. Catal.,75 2, 1991, pp. 267-280.

Hamid A. Al-Megren, Sergio L. Gonzalez-Cortes, Tiancun Xiao, Malcolm L.H. Green, A comparative study of the catalytic performance of Co—Mo and Co(Ni)—W carbide catalysts in the hydrodenitrogenation (HDN) reaction of pyridine, Applied Catalysis A: General 329 (2007) 36-45.

Sajkowski, D. J., Oyama, S. T.,; Catalytic hydrotreating by molybdenum carbide and nitride unsupported Mo2N and Mo2C/Also3; Appl. Catal. A, 134, 1996, pp. 339-345.

Zahidi, E.M., Oudghiri-Hassani, H. and McBreen, P.H., Formation of thermally stable alkylidene layers on a catalytically active surface. Nature,409, 2001, pp. 1023-1026.

Pang, Min, Li, Chuang, Ding, Ling, Zhang, Jian, Su, Dangsheng, Li, Wenzhen and Liang, Changhai, Microwave-Assisted Preparation of Mo2C/CNTs Nanocomposites as Efficient Electrocatalyst Supports for Oxygen Reduction Reaction, Ind. Eng. Chem. Res., 49 (9), 2010, pp. 4169-4174.

A.G. Constant, J.M. Giraudon, G. Leclercq and L. Leclercq,; Catalytic behaviour of cobalt or ruthenium supported molybdenum carbide catalysts for FT reaction; Appl. Catal. A, 260 (2004), p. 35.

\* cited by examiner

CATALYSTS FOR CONVERTING SYNGAS INTO LIQUID HYDROCARBONS AND METHODS THEREOF

RELATED APPLICATIONS

This application claims priority from U.S. Provisional Patent Application No. 61/849,253, filed Jan. 23, 2013, the entire disclosure of which is incorporated herein by this reference.

GOVERNMENT INTEREST

This invention was made with government support under grant number DE-FG36-06GO86025 awarded by the U.S. Department of Energy. The government has certain rights in the invention.

TECHNICAL FIELD

The presently-disclosed subject matter relates to catalysts for converting syngas to liquid hydrocarbons. In particular, embodiments of the presently-disclosed subject matter relate to multi-functional catalysts that can convert syngas into liquid hydrocarbons and methods for using the catalysts.

BACKGROUND

Known catalysts and methods exist to convert synthesis gas (syngas) to fuels and chemicals. One exemplary method includes Fischer-Tropsch synthesis (FTS), but because FTS products are controlled by Anderson-Schulz-Flory (ASF) polymerization kinetics, FTS does not provide for selective formation of hydrocarbons. Also, since the hydrocarbon products contain only carbon (C) and hydrogen (H), oxygen (O) will be released as the byproducts of $CO_2$ and $H_2O$ in the FTS process, thereby decreasing the overall efficiency of the process. To improve the overall efficiency, C, H, and O can be kept in the final products, thereby increasing the utilization of syngas. Another approach is to first convert syngas to methanol over a methanol synthesis catalyst, and subsequently polymerize methanol to hydrocarbons. These known methods generally utilize nitrogen-free syngas or low-level nitrogen syngas derived from natural gas or coal, pure syngas, or other low nitrogen syngas.

In this regard, some have attempted to utilize biomass to produce energy-related products such as electricity, fuels, heat, chemicals, and other materials. Biomass can be desirable because it can be renewable. However, because the syngas from biomass gasification can contain about 50 vol % to about 60 vol % $N_2$, the nitrogen content in biomass syngas is generally too high for hydrocarbon synthesis using existing technologies. For example, catalysts designed for the syngas-to-gasoline processes have low performance with such high nitrogen content, and the operation costs of syngas compression is a significant investment.

Additionally, while the syngas from biomass and other sources is fairly clean, some impurities, such as $H_2S$, $NH_3$, and $O_2$, do exist. Such impurities in the syngas can "poison" the catalyst and thus reduce conversion efficiency. Generally, a qualified clean syngas should have minimal amounts of sulfurs, such as $H_2S$, COS, $NH_3$, and oxygen.

Accordingly, there remains a need for a high activity and high stability catalyst useful for converting syngas, including nitrogen-rich and/or biomass derived syngas (bio-syngas), into hydrocarbons. There also remains a need for multi-functional catalysts for a single-stage syngas-to-hydrocarbon process that can be utilized with nitrogen-rich bio-syngas.

DESCRIPTION OF EXEMPLARY EMBODIMENTS

Figure 1:
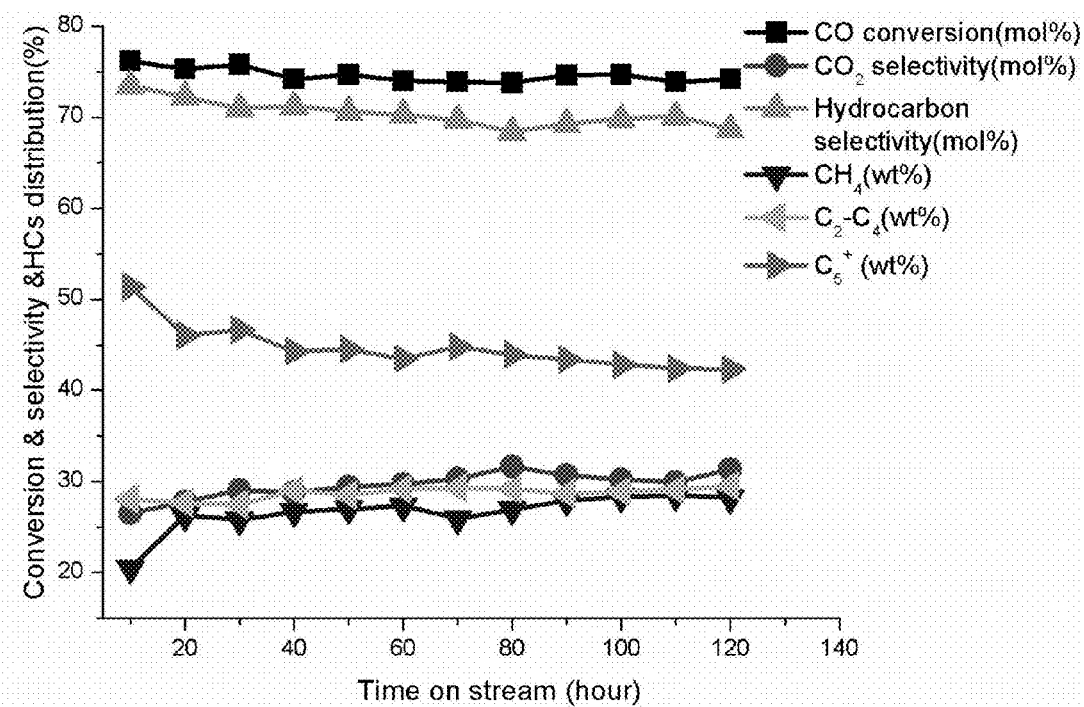
FIG. 1 includes a chart showing the effect of time on stream on CO conversion, $CO_2$ and hydrocarbon (HC) selectivity, and distribution with an embodiment of the present catalysts at 310° C., 1000 psig, and 2000 $h^{-1}$ with syngas of 19.0% $H_2$, 20.0% CO, 12.0% $CO_2$, 1.921% $CH_4$, and balance $N_2$.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods for producing liquid hydrocarbons from syngas. In some embodiments the method comprises obtaining syngas, optionally from biomass, and then contacting the syngas with a catalyst. The catalyst can then catalyze the production of liquid hydrocarbons. In some embodiments the catalyst can include a base material (support), a transition metal, and a promoter.

The term "liquid hydrocarbons" is used herein to refer to hydrocarbons that are in a liquid state at a particular temperature and pressure. In some embodiments liquid hydrocarbons are a liquid at 0° C. and ambient pressure, and in other embodiments liquid hydrocarbons are liquid at ambient temperature and pressure. In some embodiments liquid hydrocarbons refer to any $C_{4+}$ hydrocarbon. In specific embodiments liquid hydrocarbons comprise about 4 to about 20 carbon atoms per molecule, and in other embodiments liquid hydrocarbons can comprise more than 20 carbons. Further still, in some embodiments liquid hydrocarbons do not include methane, ethane, propane, butane, or combinations thereof. Some embodiments of liquid hydrocarbons may or may not include $C_{5+}$ gasoline. Those of ordinary skill will appreciate that the hydrocarbons, including liquid hydrocarbons, can include straight or branched molecules as well as cyclic or acyclic molecules.

The terms hydrocarbon and liquid hydrocarbon are also inclusive of paraffins, olefins, aromatics, and oxygenates. More specifically, exemplary liquid hydrocarbons can be selected from higher alcohols, higher esters, higher ethers, higher aldehydes, higher ketones, higher alkanes, higher alkenes, higher cycloalkanes, higher cycloalkenes, aryls, fused aryls, and combinations thereof, wherein higher can refer to any molecule having 4 or more carbons. In some embodiments the liquid hydrocarbons, including the liquid hydrocarbons described above, are an oxygenate. The term "oxygenate" is used herein to refer to a molecule having one or more oxygen atoms. In specific embodiments the liquid hydrocarbons produced by the present methods and catalysts comprise a range of about 5 wt % to about 80 wt % of oxygenates.

The "synthesis gas" (syngas) described herein is comprised primarily of hydrogen and carbon dioxide. In some embodiments the syngas is obtained from a biomass, although the term syngas is used herein to refer to both syngas that is and syngas that is not obtained from biomass. Biomass can include, but is not limited to, plant derived materials as well as metabolic waste obtained from microbes and other animals. Exemplary sources of biomass also include, but are not limited to, agricultural wastes, corn stalks, straw, seed hulls, sugarcane leavings, bagasse, nutshells, manure, wood materials, municipal waste, including waste paper and yard clippings, and specific plants grown as biomass, such as poplars, willows, switch grass, alfalfa, prairie bluestream, corn, soybean, and the like.

In this regard, the syngas in certain instances includes syngas, or biosyngas, having a relatively high concentration of nitrogen compared to syngas that is obtained from natural gas or the like. In some embodiments the biosyngas can comprise about 1 vol %, 10 vol %, 20 vol %, 30 vol %, 40 vol %, 50 vol %, 60 vol %, or any value therebetween of nitrogen. Specific embodiments can also comprise syngas that includes about 1 vol %, 10 vol %, 20 vol %, 30 vol %, 40 vol %, or any value therebetween of carbon dioxide. For example, syngas that is obtained from a gasifier that is utilizing wood chips as the feedstock can produce a syngas comprising about 20% $H_2$, about 19% CO, about 12% $CO_2$, and about 49% $N_2$. Certain embodiments described herein have the superior and unexpected result of being capable of converting syngas with relatively high concentrations of nitrogen and/or carbon dioxide into liquid hydrocarbons. Furthermore, certain embodiments described herein utilize a multi-functional catalyst (e.g., bifunctional catalyst) that can process syngas, including high-nitrogen content syngas (i.e., >20 vol %) in a single stage. On the other hand, known systems are relatively more complex, time-consuming, and expensive because high-nitrogen content syngas either cannot be processed into liquid hydrocarbons, or can only be processed into liquid hydrocarbons with two or more stages.

In some embodiments the syngas is reasonably suitable for producing liquid hydrocarbons without posing a risk of poisoning and reducing the conversion efficiency of the catalyst being used. On the other hand, in some embodiments the syngas comprises impurities that can poison a catalyst, such as $H_2S$, $NH_3$, and $O_2$. For example, syngas with about 0.5 wt % to about 1.0 wt % of oxygen, trace ammonia, sulfur, and/or tar can poison certain catalysts and possibly cause them to prematurely become ineffective at catalyzing the production of liquid hydrocarbons.

In this regard, in some embodiments, the present method for producing liquid hydrocarbons further comprises a step of cleaning syngas that is known or suspected of having impurities that could potentially poison the catalysts. In some embodiments the cleaning step comprises passing the poisoning or potentially poisoning syngas through several reactors in series that are packed with different catalysts and/or absorbents. Exemplary catalysts and absorbents include to active metals, such as copper (Cu), cobalt (Co), manganese (Mn), molybdenum (Mo), nickel (Ni), palladium (Pd), platinum (Pt), silver (Ag), and ruthenium (Rh). Exemplary catalysts and absorbents also include, but are not limited to, alumina-supported metal catalysts, 13X molsieve, active carbon, silica gel, and other high surface area materials. In specific embodiment the syngas after the cleaning step and/or from the obtaining step qualifies for total sulfurs ($H_2S+COS$) of less than 10 ppb, $NH_3$ of less than 1 ppm, and oxygen of less than 1 ppm.

As stated above, the present catalysts can comprise a base material, a transition metal, and a promoter. In some embodiments the base material is selected from a zeolite, iron, a zeolite-iron material, a cobalt-molybdenum material, a cobalt-molybdenum carbide, or a combination thereof. The zeolite can include known zeolites, and in some embodiments the zeolite can be selected from ZSM-5, ZSM-11, ZSM-12, ZSM-22, ZSM-23, ZSM-35, ZSM-48, ZSM-57, and combinations thereof. In some embodiments the zeolite is selected from a type Y zeolite.

The transition metals described herein also include salts, water-soluble halides, nitrates, amines, sulfates, acetates, carbonates, phosphates, or the like of the transition metal. Similarly, the present promoters can include alkali metals, including oxides, hydroxides, nitrates, chlorides, carbonates, sulfates, or the like of an alkali metal.

In certain embodiments the catalyst comprises a zeolite-iron base material. Specific embodiments can comprise about 40 wt % to about 80 wt % of the zeolite molecular sieve. Specific embodiments can also comprise about 2.0 wt % to about 40 wt %, 2.0 wt % to about 15.0 wt %, or about 5.0 wt % to about 15.0 wt % of iron. Both zeolite and iron comprise the zeolite-iron base material of a catalyst. The zeolite-iron base material can be prepared with different processes. For instance, the zeolite-iron base material can be prepared by precipitating iron directly onto the above-described zeolite. In other embodiments iron introduced into the zeolite by an impregnation or incipient of a transition metal. Thus, in some embodiments the catalyst comprises a base material that includes iron deposited (e.g., by precipitation) on a zeolite.

In other embodiments the zeolite-iron base material can be prepared by mixing iron oxide nanostructures with the zeolite. With regard to the iron oxide nanostructures, the term "nanostructure" is used herein to refer to any iron oxide structure that can be measured on a nanoscale (i.e., about 1 nm to about 999 nm). In other embodiments the catalyst comprises a base material that includes iron oxide nanostructures that are mixed with a zeolite. The iron oxides for use in exemplary catalysts include known and commercially available iron oxide nanostructures. In other embodiments, the present methods include preparing iron oxide nanostructures by a method selected from a sol-gel method, a hydrothermal method, an impregnation method, and a micro-emulsion method.

The present catalysts can also include a transition metal. For the zeolite-iron base material, the transition metal can be transferred directly to the base material. Exemplary methods for transferring (e.g., depositing and/or ion-exchanging) transition metals to the zeolite-iron material include one or more of a impregnation method, an ion exchange method, a hydrothermal ion exchange method, a solid state ion exchange method, a chemical vapor deposition (CVD) method, or another suitable method. In some embodiments the transition metal is added to a zeolite material before the addition of iron. Thus, in certain instances iron can be added to a zeolite to form a zeolite-iron base material by precipitating iron directly onto a transition metal containing zeolite. In yet other embodiments, iron is added to a zeolite to form a zeolite-iron base material by physically mixing iron oxide nanostructures with a zeolite that includes the transition metal.

The transition metal of a catalyst can be selected based on factors including the liquid hydrocarbon that is desired, reaction conditions, or the like. In some embodiments the transition metal for use with a zeolite-iron base material is selected from platinum (Pt), palladium (Pd), ruthenium (Ru), iridium (Ir), rhodium (Rh), molybdenum (Mo), cobalt (Co), and combinations thereof. Furthermore, the transition metals can be in the form of, but are not limited to, salts, water-soluble halides, nitrates, amine complexes, sulfates, acetates, carbonates, phosphates, or combinations thereof.

In some embodiments the incorporation of a transition metal in the catalyst can provide increased gasoline range hydrocarbon production. Likewise, the concentration of transition metal can be selected based on a various factors. Embodiments of the present catalysts can include about 0.1 wt % to about 10 wt % of a transition metal.

To prepare a catalyst that comprises transition metals, in some embodiments the transition metal is deposited on a zeolite, as described above, and then the mixture is calcined. In a specific embodiment the mixture of the transition metal and the zeolite is calcined at about 400° C. In another specific embodiment the mixture of the transition metal and the zeolite is calcined for about 3 hours to about 5 hours. The resulting material can be crushed and pelletized to tablets for use as a catalyst in a method of producing liquid hydrocarbons.

Further still, in some embodiments the present catalysts comprise a cobalt-molybdenum material as the base material. More specifically, in some embodiments the base material includes a cobalt-molybdenum carbide material. The cobalt of the base material can be obtained from cobalt-containing chemicals, such as those selected from cobalt chloride, cobalt (II) acetate, cobalt(II) acetate tetrahydrate, cobalt(II) acetylacetonate, cobalt(II) carbonate hydrate, cobalt(II) nitrate hexahydrate, cobalt(II) sulfate heptahydrate, cobalt(II,III) oxide, and the like. Furthermore, in some embodiments the molybdenum is obtained from molybdenum-containing chemicals, such as those selected from molybdenum(V) chloride, molybdenum hexacarbonyl, ammonium heptamolybdate, molybdenum(VI) tetrachloride oxide, molybdenum (VI) oxide, molybdenum(II) acetate dimer, and the like.

Embodied bimetallic cobalt-molybdenum (Co—Mo) carbide base materials have varying compositions. Exemplary Co—Mo carbide base materials can comprise about 5 wt % to about 15 wt % cobalt. Exemplary Co—Mo carbide base materials can comprise about 5 wt % to about 25 wt % molybdenum. Exemplary Co—Mo carbide base materials can also comprise about 20 wt % to about 45 wt % carbon. While those of ordinary skill will appreciate that the composition of specific base materials can vary, specific exemplary embodiments of the bimetallic Co—Mo carbide base materials include 5 wt % Co, 25 wt % Mo, and 70 wt % carbon. Another specific embodiment includes 10 wt % Co, 25 wt % Mo, and 65 wt % carbon. Another specific embodiment includes 15 wt % Co, 25 wt % Mo, and 40 wt % carbon. Another specific embodiment includes 20 wt % Co, 25 wt % Mo, and 55 wt % carbon. Another specific embodiment includes 15 wt % Co, 15 wt % Mo, and 70 wt % carbon. Another specific embodiment includes 15 wt % Co, 10 wt % Mo, and 75 wt % carbon. Another specific embodiment includes 15 wt % Co, 5 wt % Mo, and 80 wt % carbon.

In some embodiments the novel cobalt-molybdenum carbide base material is prepared by carburization of metal precursors (e.g., Co—Mo precursor) with carbon at high temperature. This can be done by a variety of processes, including, but not limited to, a two-stage reaction method developed by Newsam, a temperature programmed nitridation and topotactic carburization process, a thermal carburization process, or a direct carburization process. In one embodiment the bimetallic Co—Mo precursors were supported on carbon and prepared using a one-step incipient wetness and/or a co-precipitation method.

In some embodiments the bimetallic cobalt-molybdenum carbide base material can be prepared using a carbothermal reduction (CR) method or a carbothermal hydrogen reduction (CHR) method. The carbothermal reduction method includes the process of using helium or nitrogen as a carrier gas passed through the sample, and the reduction reaction utilizes carbon as the reductant at elevated temperature. Following the reduction process, the carbidization reaction between the reduced metal and carbon usually occurs to form transitional metal carbides. In this manner, carbothermal reduction (CR) methods can prepare embodiments of the present metal carbides. For the case of molybdenum trioxide, the following shows the reduction (1) and carbidization (2) reactions that can form $Mo_2C$.

$$MoO_3 + 3C = Mo + 3CO \qquad (1)$$

$$2Mo + C = Mo_2C \qquad (2)$$

In some embodiments the bimetallic cobalt-molybdenum carbide material can be prepared using a carbothermal hydrogen reduction (CHR) method. Hydrogen flows through the sample during the CHR process. In CHR, the reduction reaction uses hydrogen as the reductant at elevated temperature. Following the reduction process, the carbidization reaction between the reduced transitional metal and carbon occurs to form transitional metal carbides. For the case of molybdenum trioxide, the following shows the reduction (3) and carbidization (4) reactions that can for form $Mo_2C$.

$$MoO_3 + 3H_2 = Mo + 3H_2O \qquad (3)$$

$$2Mo + C = Mo_2C \qquad (4)$$

The carbon of the Co—Mo carbide base material can be derived from commercially-available carbons and/or home-synthesized carbons. Exemplary carbon resources include active carbons, carbon blacks, carbon nanotubes, carbon fibers, fullerenes, graphene, graphite, bio-char, other carbon-containing materials, and combinations thereof.

As described above, the present catalysts can include a transition metal. For some embodiments of catalysts that include a cobalt-molybdenum base material, the transition metal can be selected from iron (Fe), nickel (Ni), tungsten (W), vanadium (V), copper (Cu), silver (Ag), platinum (Pt), palladium (Pd), Ruthenium (Ru), iridium (Ir) and Rhodium (Rh), and combinations thereof. The transition metals can be in the form of, but are not limited to, salts, water-soluble halides, nitrates, amine complexes, sulfates, acetates, carbonates, phosphates, or combinations thereof. In some embodiments of the present catalysts include a cobalt-molybdenum base material and about 0.1 wt % to about 10 wt % of a transition metal. The transition metal can be added to a cobalt-molybdenum base material, or the other base materials, using the above-described methods.

In some embodiments the catalyst can further comprises a promoter in addition to the base material and, optionally, the transition metal. A promoter can be an alkali metal. Exemplary promoters include substances selected from lithium (Li), sodium (Na), potassium (K), rubidium (Rb), cesium (Cs), and combinations thereof. A promoter can also include an oxide, a hydroxide, a nitrate, a chloride, a carbonate, and/or a sulfate of the one or more alkali metals. In an exemplary embodiment the promoter is potassium hydroxide.

In some embodiments, the catalyst incorporates a promoter by an impregnation process. The concentration of a promoter will vary depending on the particular catalyst. Exemplary catalysts can include about 0.5 wt % to about 10.0 wt % of a promoter. In one particular embodiment the promoter is the last material added to form the catalyst. In some embodiments, the catalyst if formed by providing a zeolite, adding a transition metal to the zeolite, adding iron and/or iron oxide nanostructures to the zeolite, and then adding the promoter. In other embodiments the catalyst is formed by providing a cobalt-molybdenum precursor, processing the precursor to form cobalt-molybdenum carbide, adding a transition metal to the cobalt-molybdenum carbine, and then adding the promoter.

The temperature, pressure, and gas hourly space velocity (GHSV) of the syngas can be tuned in the contacting step to yield desirable liquid hydrocarbons. In some embodiments the contact step is performed at about 250° C. to about 400° C. In some embodiments the pressure in the contacting step can be about 400 psi to about 1500 psi. Furthermore, in some embodiments the contacting step is performed with the syngas having a GHSV of about $1,000^{h-1}$ to about $10,000^{h-1}$. In a specific embodiment the catalyst is such that increasing the temperature and/or pressure of the reaction generally increases carbon monoxide conversion, whereas increasing GHSV generally decreases carbon monoxide conversion. The temperature, pressure, and space velocity used when producing liquid hydrocarbons can also affect the distribution of the particular hydrocarbons that are produced.

In some methods, one or more of the temperature, pressure, space velocity, and composition of the catalyst are adjusted so that the resulting liquid hydrocarbon mixture products have a particular composition and distribution. In some embodiments the parameters are adjusted so as to yield different liquid hydrocarbon products ranging from a light gasoline boiling point range, to a diesel fuel, to a jet fuel. In some embodiments, the catalyst catalyzes the conversion of nitrogen-rich (e.g., >20%) syngas to a liquid hydrocarbon mixture enriched with a $C_5^+$ hydrocarbon fraction at low pressure. Embodiments of the present methods can be more efficient and more economical than traditional Fischer-Tropsch (FT) catalysts.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the present invention.

EXAMPLES

Example 1

This Example describes processes for making and characterizing embodiments of the present catalysts. In particular, this Example describes how to make certain iron and/or zeolite-containing catalysts, and also characterizes their ability to process synthesis gas.

An amount of 9.4 g of $PdCl_2$ was dissolved in 200 mL of deionized (DI) water and stirred for 2 hours. Then 50 g of ZSM-5 zeolite powder was added to the $PdCl_2$ solution, and $H_2SO_4$ was added in a dropwise fashion until the solution had 4.0 pH. The mixture was transferred into a 500 ml autoclave and maintained at 105-120° C. for 8-20 hours. The product was evaporated and oven-dried at 110° C. for 12 hours, then the mixture was calcined at 400° C. for 3 hours.

The obtained Pd-ZSM-5 was added to an aqueous solution containing 95 g of ferric nitrate in 500 ml of water, and the mixture was stirred at 80° C. for 12 hours. The brown products were dried at 110° C. for 5 hours, then the dried mixture was calcined at 400° C. for 5 hours. An amount of 125 mL of 2.5 wt % KOH solution was added to the resulting Fe/Pd-ZSM-5 mixture, the promoted catalyst was calcined at 300° C. for 2 hours, and then crushed and pelletized to tablets under 15 tons of force.

The synthesis gas conversion reaction was carried out in a micro-reactor of a fixed bed flow system. Three (3) grams of the catalyst were loaded to the reactor. The system was first purged by a helium flow for 30 minutes, followed by prereducing with a syngas mixture at 400° C. for 8 hours, then syngas was fed in until reaching the desired pressure with a slow adjustment of the system to the desired temperature. The reaction was operated under the following conditions: 250-400° C., a gas volume hourly space velocity (GHSV) of 500 to 5,000 $h^{-1}$, and a pressure of 500-1500 psi.

To observe the effect of temperature on the catalyst performance, temperatures studied were conducted at 290, 300, 310, 320, 330, and 350° C. Table 1 shows the variation of CO conversion and $C_1$–$C_5^+$ selectivity at various temperatures and with the other variables remaining constant. Table 1 shows that temperature influenced CO conversion was very important. CO conversion increased from 55% at 290° C. to 83% at 350° C. Table 1 also shows that the hydrocarbon distribution changed with temperature, with the light hydrocarbons being favored at higher temperatures. Higher hydrocarbons were relatively more sensitive to temperature.

TABLE 1

Effect of temperature on CO conversion, $CO_2$ and hydrocarbon selectivity, hydrocarbon distribution, and liquid hydrocarbon distribution at 1000 psig, with syngas of 19.0% $H_2$, 20.0% CO, 12.0% $CO_2$, 1.921% $CH_4$, balance $N_2$, and GHSV of 2000 $h^{-1}$, where 3 g of catalyst was used in the reaction. Time on stream of 48-100 hours.

| | Temperature (° C.) | | | | | |
|---|---|---|---|---|---|---|
| | 290 | 300 | 310 | 320 | 330 | 350 |
| | Conversion (mol %) | | | | | |
| CO | 58.2 | 65.4 | 75.4 | 83.3 | 88.9 | 93.2 |
| | Selectivity (mol %) | | | | | |
| $CO_2$ | 19.1 | 21.4 | 23.8 | 25.5 | 29.6 | 35.4 |
| Hydrocarbons | 80.9 | 78.6 | 76.2 | 74.5 | 70.4 | 64.6 |
| | Components of hydrocarbons (wt %) | | | | | |
| $CH_4$ | 18.2 | 20.5 | 21.2 | 22.1 | 23.5 | 25.7 |
| $C_2H_6$ | 8.8 | 8.2 | 9.1 | 10.2 | 10.1 | 11.9 |

TABLE 1-continued

Effect of temperature on CO conversion, $CO_2$ and hydrocarbon selectivity, hydrocarbon distribution, and liquid hydrocarbon distribution at 1000 psig, with syngas of 19.0% $H_2$, 20.0% CO, 12.0% $CO_2$, 1.921% $CH_4$, balance $N_2$, and GHSV of 2000 $h^{-1}$, where 3 g of catalyst was used in the reaction. Time on stream of 48-100 hours.

| | Temperature (° C.) | | | | | |
|---|---|---|---|---|---|---|
| | 290 | 300 | 310 | 320 | 330 | 350 |
| $C_3H_8$ | 4.8 | 5.3 | 5.9 | 6.5 | 7.8 | 9.1 |
| $C_4H_{10}$ | 11.9 | 12.1 | 10.5 | 11.7 | 9.5 | 6.2 |
| $C_5^+$ gasoline | 56.3 | 53.9 | 53.3 | 49.5 | 49.1 | 47.1 |
| Liquid Hydrocarbons Distribution (mol %) | | | | | | |
| Paraffins | 48 | 45 | 43 | 40 | 38 | 38 |
| Olefins | 21 | 20 | 20 | 18 | 15 | 14 |
| Aromatics | 31 | 35 | 37 | 42 | 47 | 48 |

Figure 2:
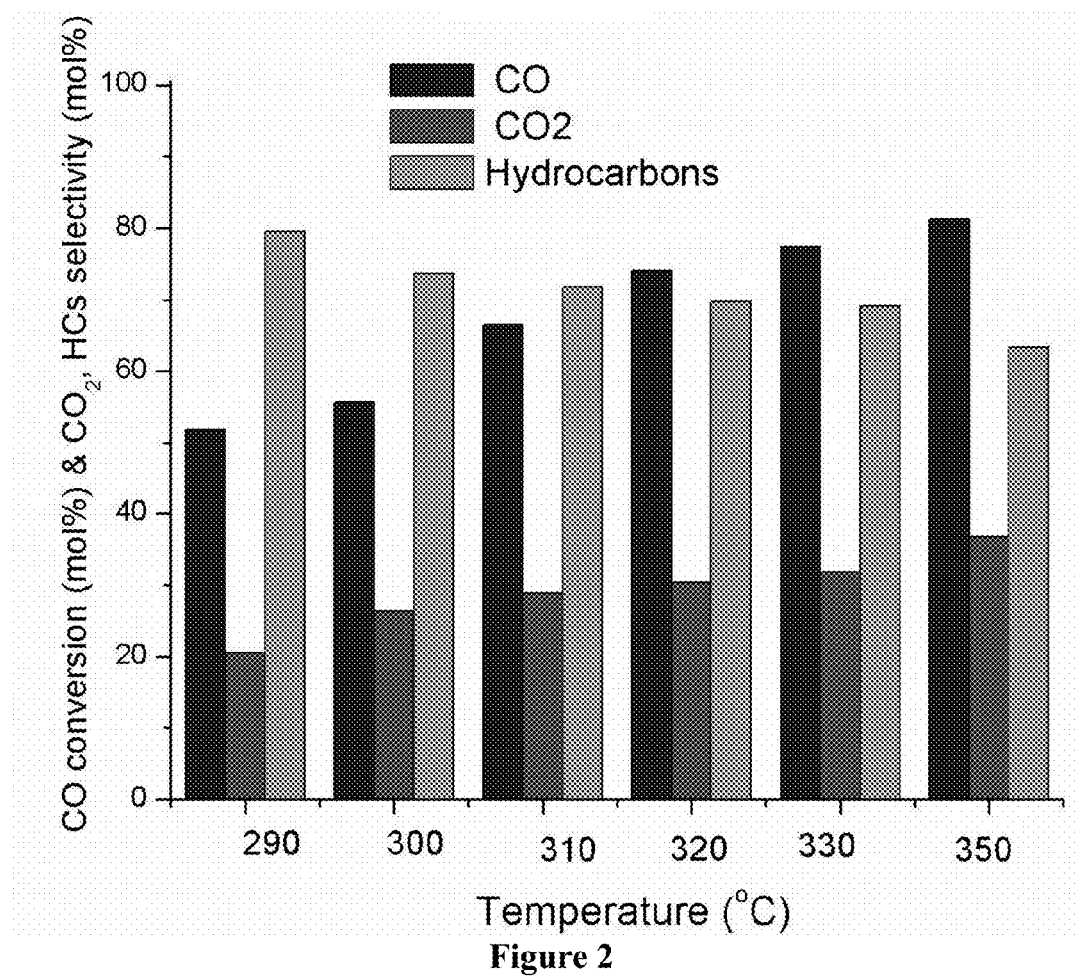
FIG. 2 includes a chart showing the effect of temperature on CO conversion and $CO_2$ and hydrocarbon selectivity with 3 g of an embodiment of the present catalysts at 1000 psig, gas hourly space velocity (GHSV) of 2000 $h^{-1}$, and time on stream of 24-28 hours with wood syngas (19.0% $H_2$, 19.0% CO, 12.0% $CO_2$, 2% $CH_4$, balance $N_2$).

Next, the influence of pressure on catalyst performance was observed. An increase in total pressure generally increased the equilibrium towards the product side and increased the conversion. The change in Gibbs free energy was negative for the system where the change in number of moles upon reaction was negative and when pressure increased. Furthermore, a change in total pressure did not affect the water gas shift reaction but did change the equilibrium product distribution. Trials under 500, 750, 1000, and 1250 psig were carried out. The other operating conditions included the following: water temperature of 310° C.; gas space velocity of 2000 $h^{-1}$, and syngas comprising 19.0% $H_2$, 20.0% CO, 12.0% $CO_2$, 1.921% $CH_4$, balance $N_2$. The effect of pressure on both CO conversion and process selectivity showed that when pressure increased, CO conversion increased (FIG. 2). Within the $C_5^+$ fraction, an effect of pressure on selectivity was observed. The increase in pressure favored the formation of $C_5^+$, while $C_1$–$C_3$ gaseous hydrocarbons decreased with increasing pressure.

TABLE 2

Effect of pressure on CO conversion, $CO_2$ and hydrocarbon selectivity, hydrocarbon distribution, and liquid hydrocarbon distribution at 310° C., with syngas of 19.0% $H_2$, 20.0% CO, 12.0% $CO_2$, 1.921% $CH_4$, balance $N_2$, and GHSV of 2000 $h^{-1}$, where 3 g of catalyst was used in the reaction. Time on stream 48-100 hours.

| Pressure (psi) | 500 | 750 | 1000 | 1250 |
|---|---|---|---|---|
| Conversion (mol %) | | | | |
| CO | 66.9 | 68.4 | 75.4 | 80.2 |
| Selectivity (mol %) | | | | |
| $CO_2$ | 24.6 | 24.1 | 23.8 | 23.5 |
| Hydrocarbons | 75.4 | 75.9 | 76.2 | 76.5 |
| Components of hydrocarbons (wt %) | | | | |
| $CH_4$ | 29.7 | 23.5 | 21.2 | 20.1 |
| $C_2H_6$ | 8.7 | 8.5 | 9.1 | 8.2 |
| $C_3H_8$ | 4.5 | 5.3 | 5.9 | 4.5 |
| $C_4H_{10}$ | 10.9 | 12.1 | 10.5 | 11.7 |
| $C_5^+$ gasoline | 46.2 | 50.6 | 53.3 | 55.5 |
| Liquid Hydrocarbons Distribution (mol %) | | | | |
| Paraffins | 43.9 | 44.5 | 43 | 42.1 |
| Olefins | 22.5 | 23 | 20 | 16.4 |
| Aromatics | 33.6 | 33.5 | 37 | 41.5 |

Figure 3:
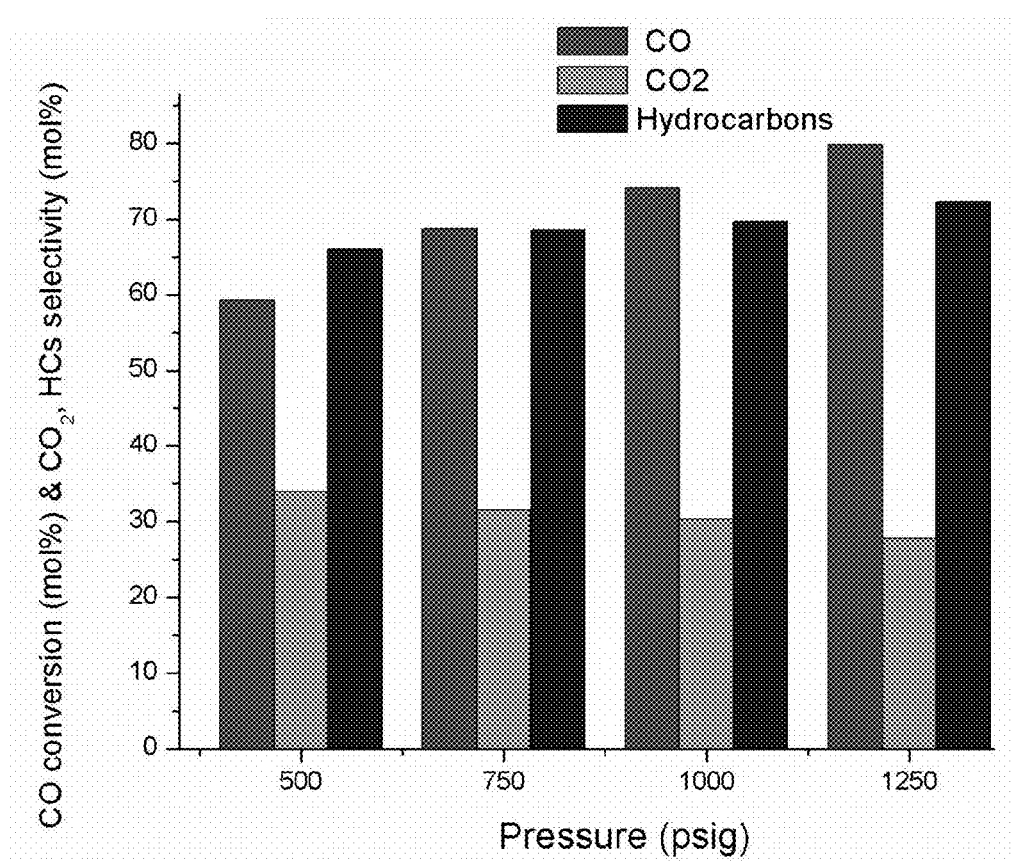
FIG. 3 includes a chart showing the effect of pressure on CO conversion and $CO_2$ and hydrocarbon selectivity with 3 g of an embodiment of the present catalysts at GHSV of 2000 $h^{-1}$, 310° C., and time on stream of 24-48 hours with wood syngas.

Next, the influence of space velocity on the catalyst performances was observed with different GHSVs of 500, 1000, 2000, 2500, and 3000 $h^{-1}$, while the remaining operating conditions were maintained at 310° C., 1000 psig, CO/$H_2$=1. The effect of the space velocity on CO conversion and hydrocarbon distribution showed that when the space velocity increased, CO conversion decreased (FIG. 3). At the same time, $C_5^+$ selectivity also decreased. It can be concluded that CO conversion decreased with the increasing of space velocity. Space time had an effect on product distribution, as it was observed that the yields of hydrocarbons decreased with increasing space velocity. The gasoline fraction ($C_5^+$) decreased with increasing space velocity.

TABLE 3

Effect of gas hourly space velocity (GHSV) on CO conversion, $CO_2$ and hydrocarbon selectivity, hydrocarbon distribution, and liquid hydrocarbon distribution at 310° C., 1000 psi, with syngas of 19.0% $H_2$, 20.0% CO, 12.0% $CO_2$, 1.921% $CH_4$, and balance $N_2$, where 3 g of catalyst was used in the reaction.

| GHSV (h-1) | 1000 | 2000 | 3000 | 4000 | 5000 |
|---|---|---|---|---|---|
| Conversion (mol %) | | | | | |
| CO | 88.2 | 80.4 | 75.4 | 73.3 | 68.9 |
| Selectivity (mol %) | | | | | |
| $CO_2$ | 28.3 | 25.7 | 23.8 | 20.5 | 21.6 |
| Hydrocarbons | 71.7 | 74.3 | 76.2 | 79.5 | 78.4 |
| Components of hydrocarbons (wt %) | | | | | |
| $CH_4$ | 14.3 | 17.5 | 21.2 | 22.5 | 23.8 |
| $C_2H_6$ | 3.5 | 4.2 | 9.1 | 10.7 | 10.3 |
| $C_3H_8$ | 2.1 | 4.7 | 5.9 | 7.5 | 7.1 |
| $C_4H_{10}$ | 7.2 | 8.6 | 10.5 | 10.7 | 10.5 |
| $C_5^+$ gasoline | 72.9 | 65 | 53.3 | 48.6 | 48.3 |
| Liquid Hydrocarbons Distribution (mol %) | | | | | |
| Paraffins | 40 | 43 | 43 | 42 | 45 |
| Olefins | 15 | 17 | 20 | 21 | 23 |
| Aromatics | 45 | 40 | 37 | 37 | 32 |

The role of syngas composition on the catalyst performances was also observed. Synthesis gas composition can, in some instances, affect both reaction rates and activity. It was found that the catalyst had a relatively high activity and selectivity in producing liquid hydrocarbons when running with nitrogen-rich syngas.

TABLE 4

Effect of syngas composition on CO conversion, $CO_2$ and hydrocarbon selectivity, hydrocarbon distribution, and liquid hydrocarbon distribution at 310° C., 1000 psig, and GHSV of 2000 $h^{-1}$, where 3 g of catalyst was used in the reaction.

| Feed gas components: | 49.64% $H_2$, 50.36% CO. | 20.1% $H_2$, 19.9% CO, balance $N_2$. | 19.0% $H_2$, 20.0% CO, 12.0% $CO_2$, 1.921% $CH_4$, balance $N_2$. | 40.054% $H_2$, 19.98% CO, 11.99% $CO_2$, 2.006% $CH_4$, balance $N_2$. |
|---|---|---|---|---|
| Conversion (mol %) | | | | |
| CO | 85.5 | 78.9 | 75.4 | 77.2 |
| Selectivity (mol %) | | | | |
| $CO_2$ | 23.5 | 26.8 | 23.8 | 27.7 |
| Hydrocarbons | 76.5 | 73.2 | 76.2 | 72.3 |

TABLE 4-continued

Effect of syngas composition on CO conversion, $CO_2$ and hydrocarbon selectivity, hydrocarbon distribution, and liquid hydrocarbon distribution at 310° C., 1000 psig, and GHSV of 2000 $h^{-1}$, where 3 g of catalyst was used in the reaction.

| Feed gas components: | 49.64% $H_2$, 50.36% CO. | 20.1% $H_2$, 19.9% CO, balance $N_2$. | 19.0% $H_2$, 20.0% CO, 12.0% $CO_2$, 1.921% $CH_4$, balance $N_2$. | 40.054% $H_2$, 19.98% CO, 11.99% $CO_2$, 2.006% $CH_4$, balance $N_2$. |
|---|---|---|---|---|
| Components of hydrocarbons (wt %) | | | | |
| $CH_4$ | 16.5 | 22.3 | 21.2 | 25.5 |
| $C_2H_6$ | 7.8 | 8.5 | 9.1 | 7.2 |
| $C_3H_8$ | 4.9 | 4.3 | 5.9 | 6.8 |
| $C_4H_{10}$ | 10.3 | 12.5 | 10.5 | 15.7 |
| $C_5^+$ gasoline | 60.5 | 52.4 | 53.3 | 44.7 |
| Liquid Hydrocarbons Distribution (mol %) | | | | |
| Paraffins | 41 | 44 | 43 | 47 |
| Olefins | 14 | 21 | 20 | 15 |
| Aromatics | 45 | 35 | 37 | 38 |

The effect of time on stream on the performance of the catalyst was observed at 310° C. over a period of 120 hours. The evolution of CO conversion and hydrocarbon distribution with time on stream are shown in FIG. 1 for the exemplary catalyst. The activity of the catalyst reached a steady state after a period of approximately 20 hours under operating conditions. Time-on-stream results showed the catalyst was stable. CO conversion reached 74% after 20 hours run at 310° C., and kept constant after 120 hours run.

Figure 4:
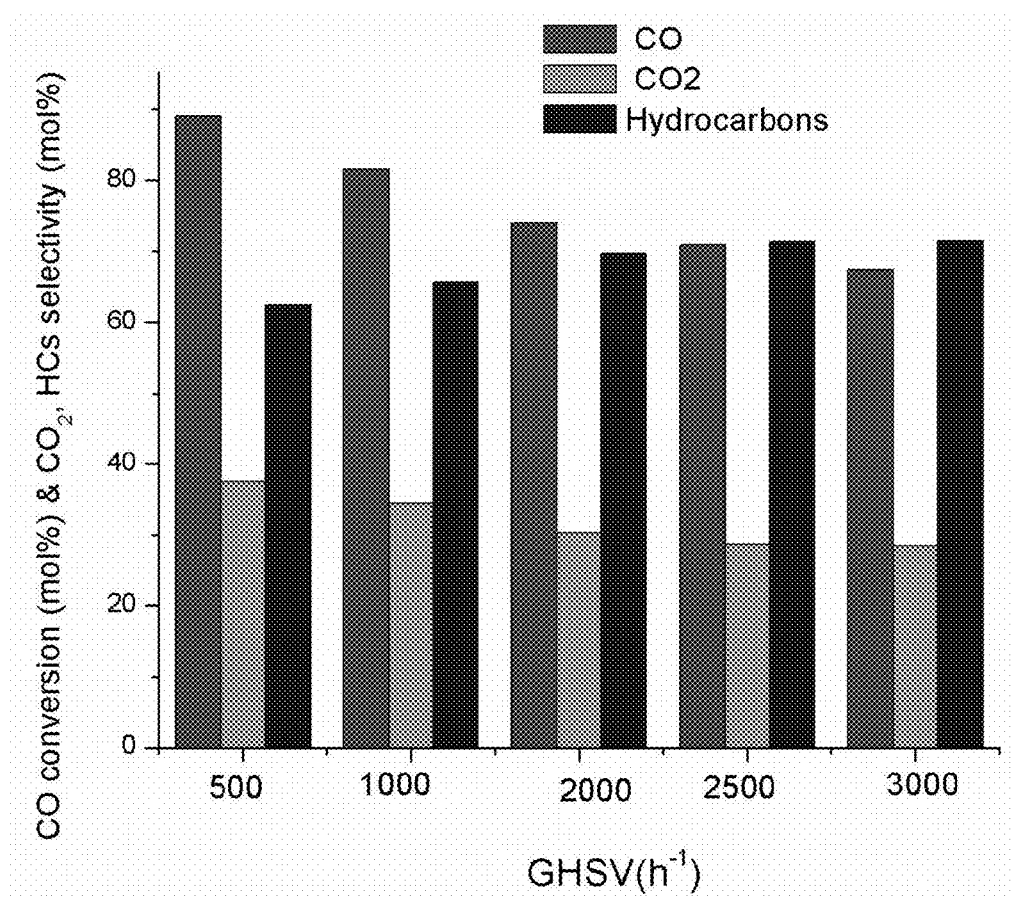
FIG. 4 includes a chart showing the effect of gas hourly space velocity (GHSV) on CO conversion and $CO_2$ and hydrocarbon selectivity with 3 g of an embodiment of the present catalysts at 310° C. and 1000 psi with wood syngas.
Figure 5:
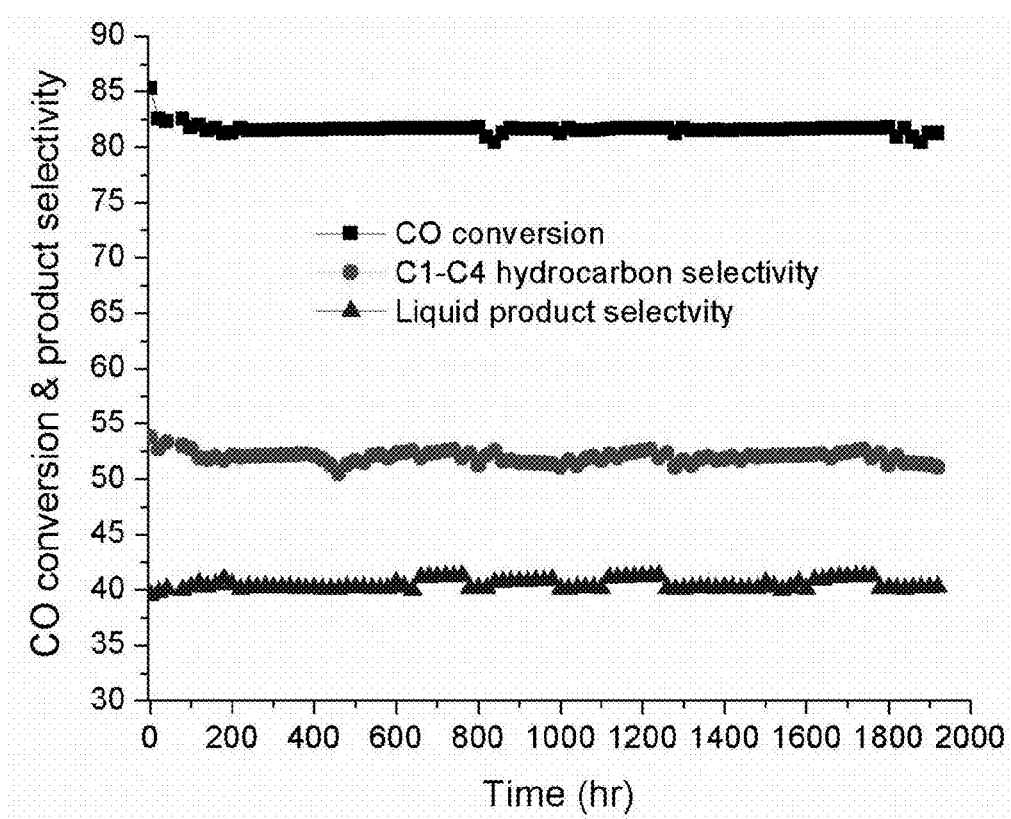
FIG. 5 includes a chart showing the effect of time on stream on CO conversion, light hydrocarbon selectivity, and liquid product selectivity with an embodiment of a Co—Mo bimetallic carbide-based catalyst at 380° C., 1000 psig, and 3000 $h^{-1}$ with syngas of 50.0% $H_2$ and 50.0% CO.

Wood syngas activity was also observed. A downdraft gasifier produced biomass syngas (bio-syngas) from wood chips and other biomass. The syngas from the gasifier contained about 20% $H_2$, 19% CO, 12% $CO_2$, and 49% $N_2$ if wood chips were used as the feedstock. In addition to the gases listed above, the bio-syngas also contained some tars, ammonia, $H_2S$, trace oxygen, and particulate impurities. Bio-syngas was cleaned by bubbling the gas through water-containing tanks before compressed the gas up to 1800 psi. The compressed wood syngas was fed to a fixed bed reactor for liquid hydrocarbon production. The wood syngas activity and selectivity was similar to that of the simulator syngas (i.e., 19.0% $H_2$, 19.0% CO, 12.0% $CO_2$, 1.921% $CH_4$, balance $N_2$) (FIGS. 2-4). Liquid product samples were collected and analyzed. The composition of the gasoline phase was also similar to the simulator syngas, except there were more aromatics and less olefins in the wood syngas product.

As a comparison, an embodiment of a catalyst that comprises nano iron oxide particles was also prepared, and its performance as the FTS catalyst was observed. Nano-structured iron particles were prepared by sol-gel, hydrothermal, impregnation, or micro-emulsion techniques. The prepared nano-structured iron oxide particle had a size of less than 50 nm. Iron chemicals were selected from $Fe(NO_3)_3$, $FeCl_2$, $FeCl_3$, $Fe(CO)_5$, and other iron-containing chemicals. Nano iron catalysts were examined for FTS to produce hydrocarbon fuels from bio-syngas produced by the downdraft gasifier (Table 5). Nano iron materials showed 75-80% CO conversion and 50-60% of liquid fuel selectivity. The liquid fuel product distribution was 30-50% olefins, 5-10% aromatics, 1% oxygenates, and 30-50% paraffins.

TABLE 5

Nano iron oxide catalyst CO conversion, $CO_2$ and hydrocarbon selectivity, hydrocarbon distribution, and liquid hydrocarbon distribution at 280° C., with syngas of 19.0% $H_2$, 20.0% CO, 12.0% $CO_2$, 1.921% $CH_4$, balance $N_2$, 1000 psig, and GHSV of 2000 $h^{-1}$.

| Conversion (mol %) | |
|---|---|
| CO | 75.3 |
| Selectivity (mol %) | |
| $CO_2$ | 20.2 |
| Hydrocarbons | 79.8 |
| Components of hydrocarbons (wt %) | |
| C1-C4 | 47 |
| $C_5^+$ | 53 |
| Liquid Hydrocarbons Distribution (mol %) | |
| Oxygenates | 1 |
| Paraffins | 55 |
| Olefins | 36 |
| Aromatics | 8 |

Next, an exemplary catalyst was prepared that included both the nano iron oxide particles and 3% wt of the Pd/ZSM-5. The nano-structured iron oxide was commercially available with a size of less than 50 nm. In the same manner as described above, Pd was introduced onto the zeolite by an impregnation process. An amount of 8 g of the commercial nano iron oxide was milled with 50 g of 5 wt % Pd/ZSM-5 for 10 hours. Then the mixture was impregnated in 125 mL 2.5% KOH solution and the promoted catalyst was dried at 110° C. for 10 hours and calcined at 400° C. for 5 hours in air. The catalyst was grounded and pelletized for testing at 310° C., 1000 psig, and 2000 $h^{-1}$ with syngas of 19.0% $H_2$, 20.0% CO, 12.0% $CO_2$, and 1.921% CH4, balance $N_2$. As shown in Table 6, the catalyst showed 76.5% CO conversion, 74.8% hydrocarbon selectivity, and 56% by weight of a $C_5+$ gasoline fraction.

TABLE 6

Nano iron oxide and Pd/ZSM-5 catalyst CO conversion, $CO_2$ and hydrocarbon selectivity, hydrocarbon distribution, and liquid hydrocarbon distribution at 310° C., with syngas of 19.0% $H_2$, 20.0% CO, 12.0% $CO_2$, 1.921% $CH_4$, balance $N_2$, 1000 psig, and GHSV of 2000 $h^{-1}$, where 3 g of catalyst was used in the reaction.

| Conversion (mol%) | |
|---|---|
| CO | 76.5 |
| Selectivity (mol %) | |
| $CO_2$ | 25.2 |
| Hydrocarbons | 74.8 |
| Components of hydrocarbons (wt %) | |
| $CH_4$ | 20.9 |
| $C_2H_6$ | 9.6 |
| $C_3H_8$ | 6.2 |
| $C_4H_{10}$ | 7.3 |
| $C_5^+$ gasoline | 56.0 |
| Liquid Hydrocarbons Distribution (mol %) | |
| Paraffins | 45.0 |
| Olefins | 22.3 |
| Aromatics | 32.7 |

Furthermore, an exemplary iron/ZSM-5 catalyst was manufactured and its properties were observed. First, 95 g of ferric nitrate was dissolved in 500 ml of DI water and then was stirred for 30 minutes. An aqueous solution was obtained.

Then, 50 g of calcined ZSM-5 was added to the solution, the mixture was stirred at 80° C. overnight, the brown products were dried at 110° C. for 5 hours, and then the dried mixture was calcined at 400° C. for 5 hours. The catalyst was grounded and pelletized for testing at 310° C., 1000 psig, 2000 h$^{-1}$ with syngas of 19.0% $H_2$, 20.0% CO, 12.0% $CO_2$, and 1.921% CH4, balance $N_2$. This catalyst gave 65.3% CO conversion, 69.8% hydrocarbon selectivity, and 46.9 wt % $C_5$+ gasoline fraction.

TABLE 7

Iron/ZSM-5 catalyst CO conversion, $CO_2$ and hydrocarbon selectivity, hydrocarbon distribution, and liquid hydrocarbon distribution at 310° C., with syngas of 19.0% $H_2$, 20.0% CO, 12.0% $CO_2$, 1.921% $CH_4$, balance $N_2$, 1000 psig, and GHSV of 2000h$^{-1}$, where 3 g of catalyst was used in the reaction.

| Conversion (mol %) | |
|---|---|
| CO | 65.3 |
| Selectivity (mol %) | |
| $CO_2$ | 30.2 |
| Hydrocarbons | 69.8 |
| Components of hydrocarbons (wt %) | |
| $CH_4$ | 27.2 |
| $C_2H_6$ | 14.3 |
| $C_3H_8$ | 6.5 |
| $C_4H_{10}$ | 5.1 |
| $C_5^+$ gasoline | 46.9 |
| Liquid Hydrocarbons Distribution (mol %) | |
| Paraffins | 40.1 |
| Olefins | 30.8 |
| Aromatics | 29.1 |

Lastly, several exemplary catalysts were manufactured in a similar procedure described above to prepare the catalyst that includes palladium and iron (e.g., Tables 1-4). However, instead of palladium, rhodium, platinum, ruthenium, cobalt, or molybdenum were impregnated into the zeolite. This Example also describes conversion reactions of synthesis gas carried out with these exemplary catalysts that comprise rhodium, platinum, ruthenium, cobalt, or molybdenum. The results of the conversion reactions are shown in Table 8.

The catalyst containing 1.0 wt % of rhodium was prepared by depositing rhodium nitrate over ZSM-5. The catalyst containing 1.0 wt % of ruthenium was prepared by depositing ruthenium trichloride over ZSM-5. The catalyst containing 1 wt % of platinum was prepared by depositing chloroplatinic acid over ZSM-5. The catalyst containing 3 wt % of Mo was prepared by depositing ammonium molybdate hydrate over ZSM-5. The catalyst containing 3 wt % of cobalt was prepared by depositing cobalt nitrate over ZSM-5. The results for these catalysts suggested that adding metals on an iron component may provide an improvement in the production of hydrocarbons from syngas.

TABLE 8

Noble metal catalyst CO conversion, $CO_2$ and hydrocarbon selectivity, hydrocarbon distribution, and liquid hydrocarbon distribution at 310° C., with syngas of 19.0% $H_2$, 20.0% CO, 12.0% $CO_2$, 1.921% $CH_4$, balance $N_2$, 1000 psig, and GHSV of 2000 h$^{-1}$, where 3 g of catalyst was used in the reaction.

| Metal | 1 wt % Rh | 1 wt % Ru | 1 wt % Pt | 3 wt % M | 3 wt % C |
|---|---|---|---|---|---|
| Conversion (mol %) | | | | | |
| CO | 81.6 | 78.5 | 77.3 | 68.2 | 79.3 |
| Selectivity (mol %) | | | | | |
| $CO_2$ | 14.9 | 19.8 | 25.3 | 33.0 | 27.2 |
| Hydrocarbons | 85.1 | 80.2 | 74.7 | 67.0 | 72.8 |
| Components of hydrocarbons (wt %) | | | | | |
| $CH_4$ | 18.3 | 25.3 | 20.4 | 30.7 | 36.6 |
| $C_2H_6$ | 4.6 | 10.5 | 11.0 | 18.2 | 18.5 |
| $C_3H_8$ | 3.9 | 4.3 | 5.3 | 7.5 | 10.3 |
| $C_4H_{10}$ | 3.2 | 3.5 | 4.5 | 6.3 | 4.5 |
| $C_5^+$ gasoline | 70.0 | 56.4 | 58.8 | 37.3 | 30.1 |
| Liquid Hydrocarbons Distribution (mol %) | | | | | |
| Paraffins | 50.8 | 49.8 | 45.0 | 43.0 | 45.5 |
| Olefins | 15.3 | 15.9 | 21.5 | 16.2 | 18.6 |
| Aromatics | 33.9 | 34.3 | 33.5 | 40.8 | 35.9 |

Example 2

This Example describes processes for making and characterizing embodiments of the present catalysts. In particular, this Example describes how to make certain cobalt-molybdenum (Co—Mo) based catalysts, and also characterizes their ability to process synthesis gas.

To first prepare the bimetallic Co—Mo precursors, an aqueous solution of ammonium heptamolybdate and cobalt nitrate was prepared with a Co/Mo molar ratio 1:1. This aqueous solution was prepared by adding 7.36 g of ammonium heptamolybdate to 20 mL DI water. The solution was heated to 80° C. and stirred until a clear, transparent solution was obtained. The solution was then cooled to 40° C., where 12.12 g of cobalt nitrate were added to the ammonium heptamolybdate solution. The mixture was stirred until a transparent solution was obtained. The obtained bimetallic salt solution then was added in a dropwise fashion to a beaker containing 10 g of active carbon support and stirred continuously. The impregnation step lasted until removal of the solvent at 80° C. by evaporation. The mass obtained was further dried at 110° C. for 12 hours.

Next, the bimetallic CoMo carbide was formed from this mass by carbothermal reduction (CR) and carbothermal hydrogen reduction (CHR) processes. The dried Co—Mo (1/1 molar ratio) over active carbon precursors were transferred to a quartz reactor (1 inch O.D.). A tubular electrical furnace controlled by a temperature program was used to heat the reactor. The amount of the sample was about 20-200 g/batch. The sample was first heated at 300° C. in helium flowing at 500 mL/min for 2 hours to obtain $CoMoO_4$. The temperature was then ramped to 700 to 1100° C. with a heating rate of 1-100° C./min under either flowing helium (100-1000 mL/min) or pure $H_2$ (100-1000 mL/min). The final temperature (700-1100° C.) was held for 2 hours. The sample was quenched (trace of the oxygen in nitrogen reacted with surface Co—Mo carbide) (100-1000 mL/min) for 2 hours at room temperature.

Furthermore, for certain exemplary embodiments at least one additional transitional metal was selected as active component of the catalyst. The additional metals were selected from the salts of iron (Fe), nickel (Ni), tungsten (W), vanadium (V), copper (Cu), silver (Ag), platinum (Pt), palladium (Pd), ruthenium (Ru), iridium (Ir), and rhodium (Rh). The additional transitional contents were introduced into the catalyst system by employing an impregnation or incipient of the Co—Mo carbide by a salt solution. The salts of the transitional metals could be nitrates, chlorides, oxides, or hydroxides. The additional metal contents could also be added using prepared nanostructured metal particles by a physical mixing process. After introducing the additional transitional metals, the mixture was first dried in an oven and then was calcined under a nitrogen flow in a one-inch quartz tube reactor. The loading of the additional transitional metals was between 0.1 and 10 percent by weight.

For this Example, an exemplary catalyst was formed by dissolving 0.5 g of palladium chloride in 10 mL DI water. The solution of $PdCl_2$ was drop-wisely added to 10 g of Co—Mo bimetallic carbide obtained from the carbothermal reduction (CR) and a carbothermal hydrogen reduction (CHR) processes, and was stirred continually. The impregnation step lasted until removal of the water solvent at 80° C. by evaporation. The sample obtained was further dried at 110° C. overnight.

Next, alkali metals in the form of oxides, hydroxides, nitrates, chlorides, carbonates, or sulfates were doped to certain samples of the Co—Mo bimetallic carbide. The alkali metals included lithium (Li), sodium (Na), potassium (K), rubidium (Rb), and caesium (Cs). Thus, the catalyst prepared with or without impregnating with transition metals (e.g., palladium) could be further promoted with 1-15 wt % alkali metals by am impregnation method. The final obtained multifunctional catalyst was first calcined under nitrogen atmosphere at 350° C. for 3 hours, and was then crushed and pelletized to tablets.

For this Example, an exemplary catalyst was formed by dissolving 0.5 g of potassium hydroxide in 10 mL DI water. The solution of KOH was added dropwise to the Pd-impregnated catalyst, and was stirred continually. The impregnation step lasted until removal of the water solvent at 80° C. by evaporation. The sample obtained was further dried at 110° C. overnight.

To observe the effect of temperature on the catalyst performance, the ability of the catalyst to convert syngas to liquid hydrocarbons and oxygenates was observed at temperatures between 200° C. and 450° C. The synthesis gas conversion reaction was carried out in a micro-reactor of a fixed bed flow system. Three (3) grams of the bimetallic CoMo catalyst that was Pd-impregnated and promoted with KOH was loaded to the reactor. The system was first purged by a helium flow for 30 minutes, followed by pre-reducing with a mixture gas of $N_2$-$H_2$ (1/1) at 400° C. for 8 hours, then syngas was fed in until reaching the desired pressure with slow adjustment of the system to the desired temperature. The reaction was operated under the following conditions: 200° C. to 450° C., a gas volume hourly space velocity (GHSV) of 500 to 5,000 $h^{-1}$, and a pressure of 200 psi to 1200 psi.

Thus, to examine temperature effects, three (3) grams of the catalyst sample were loaded to a half-inch (½") stainless steel reactor. The activity of the catalyst was investigated at 350° C., 380° C., and 410° C., 1000 psi, and 3000 $h^{-1}$ GHSV. Table 9 shows the variation of CO conversion, $C_1$~$C_4$ light hydrocarbons and liquid product selectivity with temperature, the other variables remaining constant.

TABLE 9

Effect of temperature on CO conversion, $CO_2$, light hydrocarbon, and liquid product selectivity, oil phase product distribution, and aqueous phase product distribution with syngas of 50.0% $H_2$, 50.0% CO, 1000 psig, time on stream of 8-20 hours, and GHSV of 3000 $h^{-1}$; where 3 g of catalyst was used in the reaction.

| | Temperature (° C.) | | |
|---|---|---|---|
| | 350 | 380 | 410 |
| Conversion (%) | | | |
| CO | 75.2 | 81.2 | 85.2 |
| Selectivity (%) | | | |
| $CO_2$ | 5.3 | 7.5 | 8.8 |
| C1-C4 Hydrocarbons | 38.7 | 40.3 | 43.2 |
| Liquid products | 56 | 52.2 | 48 |
| Liquid products oil/aqueous ratio (by weight) | 0.5/0.5 | 0.6/0.4 | 0.6/0.4 |

| | Components of Liquid Product (%) | | | | | |
|---|---|---|---|---|---|---|
| | Oil Phase | Aqueous Phase (40 wt % $H_2O$) | Oil Phase | Aqueous Phase (43 wt % $H_2O$) | Oil Phase | Aqueous Phase (48 wt % $H_2O$) |
| $C_5^+$ Hydrocarbons | 20.5 | — | 26.8 | — | 68.2 | — |
| $C_2^+$ alcohols | 40.2 | 60 | 30.7 | 56 | 7.5 | 53 |
| Esters | 16.3 | 15.2 | 24.9 | 19.8 | 14.1 | 11.5 |
| Aldehydes and ketones | 21.8 | 23.5 | 14.9 | 21.4 | 7.7 | 34.3 |
| Other oxygenates | 1.2 | 1.3 | 2.7 | 2.8 | 2.5 | 1.2 |

Next, the influence of pressure on catalyst performance was observed. Pressured were varied from about 200 psig to about 1000 psig. The catalyst was analyzed at a temperature of 310° C., gas space velocity of 3000 h$^{-1}$, and with syngas of 50.0% H$_2$, 50.0% CO. For this embodiments, CO conversion and process selectivity increased when pressure increased.

TABLE 10

Effect of pressure on CO conversion, CO$_2$ and hydrocarbon selectivity, hydrocarbon distribution, and liquid hydrocarbon distribution with syngas of 50.0% H$_2$, 50.0% CO, 380° C., time on stream of 48-100 hours, and GHSV of 3000 h$^{-1}$, where 3 g of catalyst was used in the reaction.

|  | Pressure (psi) | | |
| --- | --- | --- | --- |
|  | 200 | 500 | 800 |
|  | Conversion (%) | | |
| CO | 65.6 | 73.8 | 75.9 |
|  | Selectivity (%) | | |
| CO2 | 9.2 | 8.5 | 6.9 |
| C1-C4 Hydrocarbons | 45.3 | 43.2 | 41.5 |
| Liquid products | 45.5 | 48.3 | 51.6 |
| Liquid products oil/aqueous ratio (by weight) | 0.45/0.55 | 0.48/0.52 | 0.55/0.45 |
| Components of Liquid Product (%) | | | | | | |
|  | Oil Phase | Aqueous Phase(40 wt % H$_2$0) | Oil Phase | Aqueous Phase(43 wt % H$_2$0) | Oil Phase | Aqueous Phase (48 wt % H$_2$0) |
| C$_5^+$ Hydrocarbons | ~100 | — | ~100 | — | 92.0 | — |
| C$_2^+$ alcohols | — | 55.0 | — | 53.0 | 2.0 | 55.0 |
| Esters | — | 2.0 | — | 2.5 | 0.5 | 10.5 |
| Aldehydes and ketones | — | 40.0 | — | 43.5 | 5.0 | 33.5 |
| Other oxygenates | — | 3.0 | — | 1.0 | 0.5 | 1.0 |

Further still, the impact of space velocity on the catalyst performance was observed. Experiments were completed with GHSV of 1000, 3000, and 5000 h$^{-1}$, and the remaining operating conditions were maintained at 380° C., 3000 psig, and CO/H$_2$=1. The effect of the space velocity on CO conversion and hydrocarbon distribution showed that when the space velocity increased CO conversion decreases for this catalyst.

TABLE 11

Effect of gas hourly space velocity (GHSV) on CO conversion, CO$_2$ and hydrocarbon selectivity, hydrocarbon distribution, and liquid hydrocarbon distribution with syngas of 19.0% H$_2$, 20.0% CO, 12.0% CO$_2$, 1.921% CH$_4$, balance N$_2$, 100 psi, and 380° C., time on, c.

|  | GHSV (h$^{-1}$) | | |
| --- | --- | --- | --- |
|  | 1000 | 3000 | 3000 |
|  | Conversion (%) | | |
| CO | 85.3 | 81.2 | 77.5 |
|  | Selectivity (%) | | |
| CO$_2$ | 9.8 | 7.5 | 7.1 |
| C1-C4 Hydrocarbons | 40.5 | 40.3 | 42.8 |
| Liquid products | 50.3 | 52.2 | 50.1 |
| Liquid products oil/aqueous ratio (by weight) | 0.6/0.4 | 0.6/0.4 | 0.5/0.5 |
| Components of Liquid Product (%) | | | | | | |
|  | Oil Phase | Aqueous Phase(40 wt % H$_2$O) | Oil Phase | Aqueous Phase(43 wt % H$_2$O) | Oil Phase | Aqueous Phase(48 wt % H$_2$O) |
| C$_5^+$ Hydrocarbons | 33.5 | — | 26.8 | — | 21.5 | — |
| C$_2^+$ alcohols | 21.6 | 47 | 30.7 | 56 | 38.2 | 65 |
| Esters | 28.9 | 22.7 | 24.9 | 19.8 | 18.1 | 11.3 |
| Aldehydes and ketones | 15.1 | 28.5 | 14.9 | 21.4 | 21.5 | 21.9 |
| Other oxygenates | 0.9 | 1.8 | 2.7 | 2.8 | 0.7 | 1.8 |

The impact of syngas composition on the catalyst performance was also observed. Synthesis gas composition can affect higher hydrocarbon synthesis. It can affect both reaction rates and activity. It was found that the catalyst has relatively high activity and selectivity in producing liquid hydrocarbons when running even with nitrogen-rich syngas.

TABLE 12

Effect of syngas composition on CO conversion, $CO_2$ and hydrocarbon selectivity, hydrocarbon distribution, and liquid hydrocarbon distribution at 310° C., 1000 psig GHSV of 3000 $h^{-1}$; where 3 g of Co—Mo catalyst that was Pd-impregnated and promoted with KOH was used in the reaction

| | Feed gas components: | | |
|---|---|---|---|
| | 50.0% $H_2$, 50.0% CO | 67.0% $H_2$, 33.0% CO | 19.0% $H_2$, 20.0% CO, 12.0% $CO_2$, 1.921% $CH_4$, balance $N_2$ |
| Conversion | | | |
| CO | 81.2 | 83.6 | 79.5 |
| Selectivity (%) | | | |
| $CO_2$ | 7.5 | 8.4 | 5.7 |
| C1-C4 Hydrocarbons | 40.3 | 45.5 | 40.8 |
| Liquid products | 52.2 | 46.1 | 53.5 |
| Liquid products oil/aqueous ratio (by weight) | 0.6/0.4 | 0.5/0.5 | 0.55/0.45 |

| Components of Liquid Product (%) | | | | | | |
|---|---|---|---|---|---|---|
| | Oil Phase | Aqueous Phase(43 wt % $H_2O$) | Oil Phase | Aqueous Phase(39 wt % $H_2O$) | Oil Phase | Aqueous Phase(45 wt % $H_2O$) |
| $C_5^+$ Hydrocarbons | 26.8 | — | 29.3 | — | 27.5 | — |
| $C_2^+$ alcohols | 30.7 | 56 | 31.5 | 65 | 31.7 | 59 |
| Esters | 24.9 | 19.8 | 17.5 | 15.8 | 19.3 | 12.5 |
| Aldehydes and ketones | 14.9 | 21.4 | 20.6 | 19.8 | 21.5 | 27.0 |
| Other oxygenates | 2.7 | 2.8 | 1.1 | 1.3 | 1.7 | 1.5 |

The effect of time on stream on the performance of the catalyst was studied at 380° C. over a period of 1960 hours. The evolution of CO conversion as well as light hydrocarbon and liquid product selectivity with time on stream are shown in FIG. 1 for the Co—Mo bimetallic carbide-based catalyst. The activity of the Pd-impregnated and KOH-promoted catalyst reached a steady state after a period of about 40 hours under operating conditions. Time on stream results showed that the exemplary catalyst was stable. CO conversion reached 81% after 40 hours run at 380° C., and kept constant after 1960 hours run.

As a comparative example, the Co—Mo bimetallic carbide catalyst that was not impregnated or promoted was tested at 380° C., 1000 psig, 3000 $h^{-1}$ with syngas of 50.0% $H_2$, 50.0% CO. This catalyst gave 51.2% CO conversion, 61.7% light hydrocarbon selectivity, and 26.9 wt % liquid product selectivity.

TABLE 13

Performance of the catalyst that is not impregnated with transition metal or promoted with an alkali metal oxide, with syngas of 50.0% $H_2$, 50.0% CO, 380° C., 1000 psi, and 3000 $h^{-1}$, where 3 g of catalyst was used in the reaction.

| Conversion (%) | |
|---|---|
| CO | 51.2 |
| Selectivity (%) | |
| $CO_2$ | 11.4 |
| C1-C4 Hydrocarbons | 61.7 |

TABLE 13-continued

Performance of the catalyst that is not impregnated with transition metal or promoted with an alkali metal oxide, with syngas of 50.0% $H_2$, 50.0% CO, 380° C., 1000 psi, and 3000 $h^{-1}$, where 3 g of catalyst was used in the reaction.

| Liquid products | 26.9 |
|---|---|
| Liquid products oil/aqueous ratio (by weight) | 0.1/0.9 |

| Components of Liquid Product (%) | | |
|---|---|---|
| | Oil Phase | Aqueous Phase (67 wt % water) |
| $C_5^+$ Hydrocarbons | 38.5 | — |
| $C_2^+$ alcohols | 32.8 | 68 |
| Esters | 12.5 | 12.7 |
| Aldehydes and ketones | 14.9 | 17.5 |
| Other oxygenates | 1.3 | 1.8 |

Next, studies were performed with catalysts prepared in a similar procedure to the Pd-impregnated, KOH-promoted catalyst described above. However, instead of the palladium (Pd), rhodium, platinum, or ruthenium were deposited on to Co—Mo bimetallic carbide. Conversion reactions of the synthesis gas were carried out to obtain results as shown in Table 14.

The catalyst containing 1.0 wt % of rhodium was prepared by depositing rhodium nitrate over Co—Mo bimetallic carbide. The catalyst containing 1.0 wt % of ruthenium was prepared by depositing ruthenium trichloride over Co—Mo bimetallic carbide. The catalyst containing 1 wt % of platinum was prepared by depositing chloroplatinic acid over Co—Mo bimetallic carbide. The results for these catalysts suggested that adding the additional transitional metals on the Co—Mo bimetallic carbide may provide an improvement in the production of hydrocarbons from the syngas.

TABLE 14

Noble metal catalyst CO conversion, $CO_2$ and hydrocarbon selectivity, hydrocarbon distribution, and liquid hydrocarbon distribution at 380° C., with syngas of 50.0% $H_2$ and 50% CO, 1000 psig, and GHSV of 3000 $h^{-1}$, where 3 g of catalyst was used in the reaction.

| | Metal | | |
|---|---|---|---|
| | 1 wt % Rh | 1 wt % Ru | 1 wt % Pt |
| | Conversion (%) | | |
| CO | 85.1 | 83.5 | 82.3 |
| | Selectivity (%) | | |
| $CO_2$ | 5.8 | 7.5 | 8.2 |
| C1-C4 Hydrocarbons | 38.5 | 35.7 | 45.9 |
| Liquid products | 55.7 | 56.8 | 45.9 |
| Liquid products oil/aqueous ratio (by weight) | 0.62/0.38 | 0.6/0.4 | 0.5/0.5 |

| Components of Liquid Product (%) | | | | | | |
|---|---|---|---|---|---|---|
| | Oil Phase | Aqueous Phase(43 wt % water) | Oil Phase | Aqueous Phase(50 wt % water) | Oil Phase | Aqueous Phase(53 wt % water) |
| $C_5^+$ Hydrocarbons | 24.2 | — | 42.5 | — | 39.7 | — |
| $C_2^+$ alcohols | 32.5 | 58.5 | 26.7 | 59 | 29.5 | 58.9 |
| Esters | 28.7 | 29.3 | 14.5 | 16.7 | 15.2 | 20.7 |
| Aldehydes and ketones | 14.6 | 11.4 | 15 | 13.5 | 21.5 | 18.5 |
| Other oxygenates | 1.5 | 0.8 | 1.3 | 1.8 | 2.1 | 1.9 |

The above detailed description is presented to enable any person skilled in the art to make and use the invention. Specific details have been revealed to provide a comprehensive understanding of the present invention and are used for explanation of the information provided. These specific details, however, are not required to practice the invention, as is apparent to one skilled in the art. Descriptions of specific applications, analyses, and/or calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

The compositions and methods of the present invention are often best practiced by empirically determining the appropriate values of the operating parameters, or by conducting simulations to arrive at best design for a given application. Accordingly, all suitable modifications, combinations, and equivalents should be considered as falling within the spirit and scope of the invention.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a catalyst" includes a plurality of such catalysts, and so forth.

Unless otherwise indicated, all numbers expressing quantities of ingredients, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.
1. Haag, Werner O., and Huang, Tracy J., U.S. Pat. No. 4,279,830.
2. Woo, H. C.; Nam, I. S.; Lee, J. S.; Chung, J. S.; Kim, Y. G. J. Catal. 1993 142 672.
3. Epling, W. S.; Hoflund, G. B.; Hart, W. M.; Minahan, D. M. J. Catal. 1997 169 438.
4. Girardon, J.-S.; Quinet, E.; Griboval-Constant, A.; Chernayskii, P. A.; Gengembre, L.; Khodakov, A. Y. J. Catal. 2007 248 143.
5. Gormley, R. J.; Rao, V. U. S.; Anderson, R. R.; Schehl, R. R.; Chi, R. D. H. J. Catal. 1988 113 193.
6. Shi, B.; Davis, B. H. Appl. Catal. A: General 2004 277.
7. Chang, C. D. Lang, W. H.; Silvestri, A., U.S. Pat. No. 4,096,163, 1978.
8. Qiangu Yan, et al., *J. Phys. Chem. C,* 2008, 112 (31), pp 11847-11858.
9. Mysov, V. M.; Reshetnikov, S. I.; Stepanov, V. G.; Ione, K. G. Chem. Eng. J. 2005 107 63.
10. Comelli, R. A.; F'goli, N. S. React. Kinet. Catal. Lett. 1994 52 139.
11. Xu, D., H. Duan, et al., EnergyFuels, 2006, 20(3): 955-958.
12. Jess, A., R. Popp, et al. (1999), Applied Catalysis A: General, 186(1-2): 321-342.
13. Martinez, Agustin; Ronan, Joan; Arribas, Maria A.; Cerqueira, Henrique S.; Costa, Alexandre F. and Aguiar, Eduardo Falabella S., *J. Catal.* 2007, 249, 162.
14. Girardon, J.-S.; Quinet, E.; Griboval-Constant, A.; Chernayskii, P. A.; Gengembre, L. and Khodakov, A. Y., *J. Catal.* 2007, 248, 143.
15. Gormley, R. J.; Rao, V. U. S.; Anderson, R. R.; Schehl, R. R. and Chi, R. D. H., *J. Catal.* 1988, 113, 193.
16. Mills, G. Alex, *Fuel,* 1994, 73, 1243.
17. Morales, Fernando; de Smit, Emiel; de Groot, Frank M. F.; Visser, Tom and Weckhuysen, Bert M., *J. Catal.* 2007, 246, 91.
18. Liu, Zhong-Wen; Li, Xiaohong; Asami, Kenji and Fujimoto, K., *Appl. Catal. A: General* 2006, 300, 162.
19. Dry, M. E., *Catal. Today,* 2002, 71, 227.
20. Khodakov, A. Y.; Chu, W. and Fongarland, P., *Chem. Rev.,* 2007, 107, 1692.
21. Espinoza, R. L.; Steynberg, A. P.; Jager, B. and Vosloo, A. C., *Appl. Catal. A: General* 1999, 186, 13.
22. Bedel, L.; Roger, Anne-Cecile; Rehspringer, Jean-Luc; Zimmermann, Yvan and Kiennemann, A., *J. Catal.* 2005, 235, 279.
23. Shi, Buchang and Davis, Burtron H., *Appl. Catal. A: General* 2004, 277, 61.
24. Patzlaff, J.; Liu, Y.; Graffmann, C. and Gaube, J., *Appl. Catal. A: General* 1999, 186, 109.
25. Rightor, Edward G.; Tzou, Ming-Shin and Pinnavaia, Thomas J. *J. Catal.* 1991, 130, 29.
26. Dictor, Ronald A. and Bell, Alexis T. *J. Catal.* 1986, 97, 121.
27. Catalytic Upgrading Biosyngas From a Downdraft Gasifier to Liquid Hydrocarbons, Qiangu Yan and Fei Yu, Proceeding of 2011 AIChE Spring Meeting & 7th Global Congress on Process Safety
28. Mysov, V. M.; Reshetnikov, S. I.; Stepanov, V. G. and Ione, K. G., Chem. Eng. J. 2005, 107, 63.
29. Simard, F.; Sedrán, U. A.; Sepúlveda, J.; Fígoli, N. S.; de Lasa, H. ZnO—$Cr_2O_3$+ZSM5 Catalyst with Very Low Zn/Cr ratio for the Transformation of Synthesis Gas to Hydrocarbons. *Appl. Catal.* 1995, 125, 81
30. Chang, C. D.; Lang, W. H.; Silvestri, A., U.S. Pat. No. 4,096,163, 1978.
31. Chang, C. D.; Lang, W. H; Bell, W. K., *Chemical Energy Product Symposium Proceedings,* 1980, 1, 127.
32. Inui, T.; Takegami, Y., *Proc. Pan. Pac. Synfuels Conf* 1982, 1, 145.
33. Inui, T.; Takegami, Y., *ACS Symp. Ser.* 1982, 27, 982.
34. Yashima, T.; Yoshimura, A.; Wakuskima, Y.; Namba, S., *Proc. Pan. Pac. Synfuels Conf* 1984, 1, 130.
35. Simard, F.; Mahay, A.; Ravella, A.; Jean, G.; de Lasa, H., *Ind. Eng. Chem. Res.* 1991; 30, 1448.
36. Simard, F.; Sedran, U. A.; Sepulveda, J.; Figoli, N. S.; de Lasa, H., *Appl. Catal.* 1995, 125, 81.
37. Comelli, R. A.; Fígoli, N. S., *React. Kinet. Catal. Lett.* 1994, 52, 139.
38. Zaidi, H. A. and Pant, K. K., *Catal. Today* 2004, 96, 155.
39. Campbell, S. M.; Bibby, D. M.; Coddington, J. M. and Howe, R. F., *J. Catal.* 1996, 161, 350.
40. Odell, A. L.; Coddington, J. M. and Liddell, M. J., *J. Catal.* 1994, 147, 358.
41. Tau, Li-Min; Fort, Arthur W.; Bao, Shiqi and Davis, Burtron H., *Fuel Proc. Tech.* 1990, 26, 209.
42. Amit C. Gujar, Vamshi Krishna Guda, Michael Nolan, Qiangu Yan, HosseinToghiani, Mark G. White, Reactions of methanol and higher alcohols over H-ZSM, *Applied Catalysis A: General, Volume* 363, 2009, *Pages* 115-121
43. Levy, R. B. and Boudart, M., Platinum-like behavior of tungsten carbide in surface catalysis. *Science,* 181, 1973, pp. 547-549.
44. Ribeiro, F. H., Boudart, M., DallaBetta, R. A. and Iglesia, E., Catalytic reactions of normal-alkanes on beta-$W_2C$ and WC—the effect of surface oxygen on reaction pathways, *J. Catal.,* 130, 1991, pp. 498-513.
45. Cheng, Jinmin and Huang, Wei, Fuel Processing Technology, 91, (February 2010), pp. 185-193
46. Borowiechi, T. and Golebiowski, A., Influence of molybdenum and tungsten additives on the properties of nickel steam reforming catalysts, Catal. Lett. 25, 1994, pp. 309-313.
47. LaMont, D. C. and Thomson, W. J., The influence of mass transfer conditions on the stability of molybdenum carbide for dry methane reforming, *Appl. Catal. A,* 274, 2004, pp. 173-178.
48. Kojima, I., Miyazaki, E., Inoue, Y. and Yasumori, I., Catalysis by transition metal carbides, *J. Catal.* 73, 1982, pp. 128-135.
49. Woo, H. C., Park, K. Y., Kim, Y. G., Nam, I. S., Chung, J. S. and Lee, J. S., Mixed alcohol synthesis from carbonmonoxide and dihydrogen over potassium-promoted molybdenum carbide catalysts. *Appl. Catal.,* 75 2, 1991, pp. 267-280.
50. Lee, K. S., Abe, H., Reimer, I. A. and Bell, A. T., Hydrodenitrogenation of quinoline over high-surface-area $Mo_2N$, *J. Catal.* 139, 1993, pp. 34-40.

51. Sajkowski, D. J., Oyama, S. T., *Appl. Catal. A*, 134, 1996, pp. 339-345.
52. Zahidi, E. M., Oudghiri-Hassani, H. and McBreen, P. H., Formation of thermally stable alkylidene layers on a catalytically active surface. *Nature*, 409, 2001, pp. 1023-1026.
53. Pang, Min, Li, Chuang, Ding, Ling, Zhang, Jian, Su, Dangsheng, Li, Wenzhen and Liang, Changhai, Microwave-Assisted Preparation of $Mo_2C$/CNTs Nanocomposites as Efficient Electrocatalyst Supports for Oxygen Reduction Reaction, *Ind. Eng. Chem. Res.*, 49 (9), 2010, pp. 4169-4174.
54. A. G. Constant, J. M. Giraudon, G. Leclercq and L. Leclercq, *Appl. Catal. A*260 (2004), p. 35
55. H. C. Woo, K. Y. Park, Y. G. Kim, I. Nam, J. S. Chung and J. S. Lee, Mixed alcohol synthesis from carbon monoxide and dihydrogen over potassium-promoted molybdenum carbide catalysts, *Appl. Catal.* 75 (1991), p. 267.
56. Xiang, Minglin, Li, Debao, Xiao, Haicheng, Zhang, Jianli, Qi, Huijie, Li, Wenhuai, Zhong, Bing and Sun, Yuhan, Synthesis of higher alcohols from syngas over Fischer-Tropsch elements modified K/β-$Mo_2C$ catalysts, *Fuel*, 87, 2008, pp. 599-603.
57. Newsam, J. M., Jacobson, A. J., Mccandlish, L. E. and Polizzotti, R. S., *J. Solid State Chem.*, 75, 1988, pp. 296-300.
58. Korlann, S., Diaz, B. and Bussell, M. E., *Chem. Mater.*, 14, 2002, pp. 4049-4055.
59. Xiao, T.-C., York, A. P. E., Al-Megren, H., Williams, C. V., Wang, H.-T. and Green, M. L. H., *J. Catal.*, 202, 2001, pp. 100-108.
60. Liang, C., Ying, P. and Li, C., *Chem. Mater.*, 14, 2002, pp. 3148-3155.
61. Liang, C., Ma, W., Feng, Z. and Li, C., *Carbon*, 41, 2003, pp. 1833-1839.
62. Liang, C., Tian, F., Li, Z., Feng, Z., Wei, Z. and Li, C., *Chem. Mater.*, 15, 2003, pp. 4846-4850.
63. Wang, Xiao-Hui, Zhang, Ming-Hui, Li, Wei and Tao, Ke-Yi, Synthesis and characterization of cobalt-molybdenum bimetallic carbides catalysts, *Catalysis Today*, 131, 2008, pp. 111-117.

What is claimed is:

1. A method for producing liquid hydrocarbon from syngas, comprising:
   obtaining a syngas from a biomass;
   contacting the syngas with a catalyst to catalyze the production of the liquid hydrocarbons;
   wherein the catalyst includes a base material that includes a zeolite-iron material, a cobalt-molybdenum carbide, or a combination thereof; a transition metal; and a promoter;
   wherein the promoter is potassium hydroxide, potassium carbonate or potassium nitrate.

2. The method of claim 1, wherein the base material includes a zeolite-iron material, and wherein the transition metal is selected from platinum (Pt), palladium (Pd), ruthenium (Ru), iridium (Ir), rhodium (Rh), molybdenum (Mo), cobalt (Co), and combinations thereof.

3. The method of claim 1, wherein the zeolite-iron material includes iron oxide nanostructures.

4. The method of claim 1, wherein the base material includes a cobalt-molybdenum carbide, and wherein the transitional metal is selected from iron (Fe), nickel (Ni), tungsten (W), vanadium (V), copper (Cu), silver (Ag), platinum (Pt), palladium (Pd), Ruthenium (Ru), iridium (Ir), rhodium (Rh), and combinations thereof.

5. The method of claim 1, wherein the syngas includes about 1 vol % to about 60 vol % of nitrogen ($N_2$).

6. The method of claim 1, wherein the syngas includes about 1 vol % to about 40 vol % of carbon dioxide ($CO_2$).

7. The method of claim 1, further comprising:
   cleaning, before the obtaining step, a gasifier by packing the gasifier with one or more of alumina-supported metal catalysts, 13X molsieve, active carbon, silica gel, copper (Cu), cobalt (Co), manganese (Mn), molybdenum (Mo), nickel (Ni), palladium (Pd), platinum (Pt), silver (Ag), and ruthenium (Rh), wherein
   the syngas from the cleaning step includes less than about 10 ppb of total $H_2S$ and COS, less than 1 ppm of $NH_3$, and/or less than 1 ppm of oxygen.

8. The method of claim 1, wherein the liquid hydrocarbons are selected from higher alcohols, higher esters, higher ethers, higher aldehydes, higher ketones, and combinations thereof.

9. The method of claim 1, wherein the liquid hydrocarbons are produced from the syngas in a single stage.

10. The method of claim 1, wherein the liquid hydrocarbons include about 5 wt % to about 80 wt % of oxygenates.

11. The method of claim 1, wherein the contacting step is performed at a temperature of about 250° C. to about 400° C.

12. The method of claim 1, wherein the contacting step is performed at a pressure of about 400 psi to about 1500 psi.

13. The method of claim 1, wherein the contacting step is performed with the syngas flowing at a gas hourly space velocity (GHSV) of about $1,000^{-1}$ to about $10,000\ h^{-1}$.

14. A catalyst, comprising:
   a base material that includes a zeolite-iron material, a cobalt-molybdenum carbide, or a combination thereof;
   a transition metal; and
   a promoter;
   wherein the promoter is potassium hydroxide, potassium carbonate, or potassium nitrate.

15. The catalyst of claim 14, wherein the catalyst is a multifunctional catalyst capable of catalyzing the production of liquid hydrocarbons form syngas, and wherein the syngas includes about 1 vol % to about 60 vol % of nitrogen ($N_2$).

16. The catalyst of claim 14, wherein the catalyst comprises about 0.1 wt % to about 10.0 wt % of the transition metal.

17. The catalyst of claim 14, wherein the catalyst comprises about 0.5 wt % to about 10.0 wt % of the promoter.

18. The catalyst of claim 14, wherein the zeolite-iron material is selected from H-ZSM5, Y-zeolite, and combinations thereof.

19. The catalyst of claim 14, wherein the base material includes the zeolite-iron material, and the transition metal is selected from platinum (Pt), palladium (Pd), ruthenium (Ru), iridium (Ir), rhodium (Rh), molybdenum (Mo), cobalt (Co), and combinations thereof.

20. The catalyst of claim 14, wherein the iron includes iron oxide particles.

21. The catalyst of claim 20, wherein the catalyst comprises about 2.0 wt % to about 15.0 wt % of the iron oxide particles.

22. The catalyst of claim 14, wherein the base material includes the cobalt-molybdenum carbide, and wherein the transition metal is selected from iron (Fe), nickel (Ni), tungsten (W), vanadium (V), copper (Cu), silver (Ag), platinum (Pt), palladium (Pd), Ruthenium (Ru), iridium (Ir), rhodium (Rh), and combinations thereof.

23. The catalyst of claim 14, wherein the cobalt-molybdenum carbide is produced from a carbon selected from active carbons, carbon blacks, carbon nanotubes, carbon nano-fibers, fullerenes, graphene, graphite, bio-chars, and combinations thereof.

* * * * *